US011464809B2

(12) United States Patent
Danilkovitch et al.

(10) Patent No.: US 11,464,809 B2
(45) Date of Patent: *Oct. 11, 2022

(54) UMBILICAL TISSUE COMPOSITIONS AND METHODS OF USE

(71) Applicant: Osiris Therapeutics, Inc., Columbia, MD (US)

(72) Inventors: Alla Danilkovitch, Columbia, MD (US); Yi Duan-Arnold, Ellicott City, MD (US); Matthew Moorman, Chestertown, MD (US); Anne Lerch, Annapolis, MD (US); Jin-Qiang Kuang, Gleneig, MD (US)

(73) Assignee: OSIRIS THERAPEUTICS, INC., Columbia, MD (US)

( * ) Notice: Subject to any disclaimer, the term of this patent is extended or adjusted under 35 U.S.C. 154(b) by 214 days.

This patent is subject to a terminal disclaimer.

(21) Appl. No.: 16/840,554

(22) Filed: Apr. 6, 2020

(65) Prior Publication Data

US 2020/0390824 A1 Dec. 17, 2020

Related U.S. Application Data

(63) Continuation of application No. 15/274,100, filed on Sep. 23, 2016, now Pat. No. 10,624,931.

(60) Provisional application No. 62/222,446, filed on Sep. 23, 2015.

(51) Int. Cl.
*A61K 35/51* (2015.01)
*A61K 35/50* (2015.01)
*A01N 1/02* (2006.01)

(52) U.S. Cl.
CPC .............. *A61K 35/51* (2013.01); *A01N 1/021* (2013.01); *A61K 35/50* (2013.01)

(58) Field of Classification Search
CPC ......... A61K 35/51; A61K 35/50; A01N 1/021
See application file for complete search history.

(56) References Cited

U.S. PATENT DOCUMENTS

| 7,928,280 B2 | 4/2011 | Hariri et al. |
| 2003/0187515 A1 | 10/2003 | Hariri et al. |
| 2004/0048796 A1 | 3/2004 | Hariri et al. |
| 2008/0069895 A1 | 3/2008 | Liu et al. |
| 2015/0010506 A1 | 1/2015 | Jansen et al. |
| 2016/0030635 A1 | 2/2016 | Bhatia et al. |

FOREIGN PATENT DOCUMENTS

| EP | 2351538 | 8/2011 |
| JP | 2008200341 | 9/2008 |
| JP | 2012031127 | 2/2012 |
| JP | 2015142559 | 8/2015 |
| WO | WO 2004/060359 | 7/2004 |
| WO | WO 2004/072273 | 8/2004 |
| WO | WO 2011/031489 | 3/2011 |
| WO | WO 2012/112441 | 8/2012 |
| WO | WO 2014/027965 | 2/2014 |
| WO | WO 2016/154452 | 9/2016 |
| WO | WO 2017/053701 | 3/2017 |

OTHER PUBLICATIONS

Office Action issued in Corresponding Japanese Application No. 2018-515001, dated Oct. 5, 2020 (English Translation provided).
ASTM 06797-02, Standard Test Method for Bursting Strength of Fabrics Constant-Rate-of-Extension (CRE) Ball Burst Test. ASTM International. 2002 (3 pages).
Caputo et al., "A retrospective study of cryopreserved umbilical cord as an adjunctive therapy to promote the healing of chronic, complex foot ulcers with underlying osteomyelitis : Cryopreserved umbilical cord for complex ulcers with osteomyelitis", *Wound Repair and Regeneration* 2016, 24(5), pp. 885-893.
Chua et al., "An Open Label Prospective Pilot Study to Evaluate the Efficacy of Cryopreserved Amniotic Tissue Grafts for Chronic Nonhealing Ulcers", *Wounds* 2014, 26(5), pp. E30-E38.
Cooke et al., "Comparison of cryopreserved amniotic membrane and umbilical cord tissue with dehydrated amniotic membrane/ chorion tissue", *Journal Of Wound Care* 2014, 23(10), pp. 465-4 76.
Dhall et al., "Viable cryopreserved umbilical tissue (vCUT) reduces post-operative adhesions in a rabbit abdominal adhesion model", *Bioactive Materials* 2019, 4(1), pp. 97-106.
European Search Report dated Mar. 27, 2019 by the European Patent Office for EP Application No. 16849682.6, filed on Sep. 23, 2016 and published as 3352771 on Aug. 1, 2018 (Applicant—Osiris Therapeutics, Inc.) (8 Pages).
FDA News: "Umbilical Cord-Based Technology May Offer Hope for Diabetic Foot Ulcers 1 Jul. 31, 2014 1 FDANews", Aug. 1, 2014 (Aug. 1, 2014 ), Retrieved from the Internet: URL: https://www.fdanews.com/articles/pri_nt/166171-umbilicalcord-based-technology-may-offerhope-for-diabetic-foot-ulcers [retrieved on Mar. 14, 2019 ].

(Continued)

*Primary Examiner* — Lynn Y Fan
(74) *Attorney, Agent, or Firm* — Norton Rose Fulbright US LLP

(57) ABSTRACT

Disclosed are compositions comprising umbilical tissue, wherein the umbilical tissue comprises one or more engineered channels. Also disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells. Disclosed are methods of producing compositions comprising umbilical tissue, wherein the umbilical tissue comprises one or more engineered channels. Also disclosed are methods of treating damaged tissue comprising administering to the site of the damaged tissue compositions comprising umbilical tissue, wherein the umbilical tissue comprises one or more engineered channels.

14 Claims, 10 Drawing Sheets

(56) References Cited

OTHER PUBLICATIONS

Freytes, D.O. et al., "Biaxial Strength of Multilaminated Extracellular Matrix Scaffolds." *Biomaterials* 2004; 25(12): 2353-61.
Ghajar et al., "Mesenchymal Stern Cells Enhance Angiogenesis in Mechanically Viable Prevascularized Tissues via Early Matrix Metalloproteinase Upregulation" *Tissue Eng.* 2006, 12(10), 2875-88.
Hanselman et al., "Topical Review : Use of Fetal Tissue in Foot and Ankle Surgery", *Foot & Ankle Specialist* 2015, vol. 8, No. 4, pp. 297-304.
International Search Report and Written Opinion dated Feb. 21, 2017 by the International Searching Authority for Patent Application No. PCT/US2016/053309, which was filed on Sep. 23, 2016 and published as WO 2017/053701 on Mar. 30, 2017 (Inventor—Danilkovitch et al.; Applicant—Osiris Therapeutics, Inc.; (10 pages).
Pennati, G., "Biomechanical Properties of the Human Umbilical Cord." *Biorheology*. 2001; 38(5-6), 355-66.

Original UT   With engineered channels   Trypan blue stain for better visualization

| Fiber Orientation | Specimen # | Specimen ID | Maximum Load (N) | Displacement at Maximum Load (mm) |
|---|---|---|---|---|
| Parallel | 1 | PLC002438 | 4.30 | 14.93 |
| Parallel | 2 | PLC002413 | 3.73 | 10.64 |
| Parallel | 3 | PLC002477 | 2.25 | 13.61 |
| Parallel | 4 | PLC002413 | 4.12 | 14.22 |
| Parallel | 5 | PLC002464 | 2.54 | 7.94 |
| Parallel | 6 | PLC002464 | 3.33 | 14.04 |
| Parallel | 7 | PLC002438 | 5.37 | 7.18 |
| Parallel | 8 | PLC002413 | 4.11 | 12.39 |
| Parallel | 9 | PLC002413 | 3.26 | 9.13 |
| Perpendicular | 1 | PLC002477 | 2.61 | 21.09 |
| Perpendicular | 2 | PLC002464 | 0.95 | 17.86 |
| Perpendicular | 3 | PLC002474 | 3.24 | 18.49 |
| Perpendicular | 4 | PLC002477 | 4.61 | 16.64 |
| Perpendicular | 5 | PLC002464 | 3.85 | 14.34 |
| Perpendicular | 6 | PLC002474 | 1.38 | 15.50 |
| Perpendicular | 7 | PLC002477 | 0.68 | 9.26 |
| Perpendicular | 8 | PLC002438 | 3.26 | 4.04 |
| Perpendicular | 9 | PLC002474 | 2.98 | 3.18 |

FIG. 9

| Specimen ID | Thickness* (mm) | Max Load (N) | Displacement at max load (mm) | Max Wall Stress (MPa) | Stretch at max wall stress (mm/mm) |
|---|---|---|---|---|---|
| PLC002413 | 2.30 ± 0.44 | 9.76 | 4.59 | 0.09 | 1.86 |
| PLC002438 | 2.63 ± 0.59 | 19.58 | 3.55 | 0.12 | 1.89 |
| PLC002370 | 1.71 ± 0.66 | 12.91 | 7.78 | 0.17 | 2.24 |
| PLC002477 | 2.05 ± 0.85 | 12.40 | 5.90 | 0.13 | 2.02 |
| PLC002474 | 2.06 ± 0.76 | 15.57 | 7.22 | 0.15 | 2.21 |
| PLC002464 | 1.74 ± 0.64 | 15.05 | 6.94 | 0.18 | 2.17 |
| PLC002438 | 2.86 ± 0.66 | 19.73 | 3.64 | 0.10 | 1.90 |
| PLC002399 | 3.23 ± 0.26 | 19.20 | 5.37 | 0.09 | 2.04 |
| PLC002438 | 1.62 ± 0.40 | 16.16 | 6.05 | 0.20 | 2.08 |

FIG. 10

| Fiber Orientation | Specimen ID | Thickness* (mm) | Width* (mm) | Area (mm²) | Maximum Load (N) | Displacement at Maximum Load (mm) | Maximum Stress (MPa) | Strain at Maximum Stress (mm/mm) |
|---|---|---|---|---|---|---|---|---|
| Parallel | PLC002370 | 2.30 ± 0.58 | 6.33 ± 0.58 | 14.57 | 4.08 | 9.72 | 0.28 | 0.36 |
| Parallel | PLC002730 | 2.09 ± 0.18 | 7.00 ± 0.00 | 14.61 | 3.48 | 9.72 | 0.24 | 0.36 |
| Parallel | PLC002370 | 1.63 ± 1.40 | 7.00 ± 1.00 | 11.39 | 3.42 | 7.15 | 0.30 | 0.26 |
| Parallel | PLC002366 | 2.29 ± 0.31 | 6.33 ± 0.58 | 14.52 | 4.14 | 10.73 | 0.28 | 0.40 |
| Parallel | PLC002366 | 0.71 ± 0.27 | 8.33 ± 0.58 | 5.94 | 7.72 | 13.49 | 1.30 | 0.50 |
| Parallel | PLC002319 | 2.39 ± 0.28 | 5.33 ± 0.58 | 12.76 | 5.10 | 11.99 | 0.40 | 0.44 |
| Parallel | PLC002366 | 2.25 ± 0.25 | 5.67 ± 0.58 | 12.75 | 3.07 | 14.39 | 0.24 | 0.53 |
| Parallel | PLC002366 | 1.70 ± 0.71 | 6.00 ± 0.00 | 10.22 | 4.53 | 8.61 | 0.44 | 0.32 |
| Parallel | PLC002366 | 2.33 ± 0.20 | 5.67 ± 0.58 | 13.18 | 4.48 | 13.48 | 0.34 | 0.50 |
| Perpendicular | PLC002477 | 1.18 ± 0.23 | 6.33 ± 0.58 | 7.49 | 9.96 | 9.10 | 1.33 | 0.34 |
| Perpendicular | PLC002317 | 2.95 ± 1.00 | 7.67 ± 0.58 | 22.64 | 5.64 | 7.76 | 0.25 | 0.29 |
| Perpendicular | PLC002474 | 2.13 ± 0.27 | 7.67 ± 0.58 | 16.30 | 5.68 | 8.37 | 0.35 | 0.31 |
| Perpendicular | PLC002464 | 2.25 ± 0.78 | 6.00 ± 0.00 | 13.52 | 2.22 | 7.63 | 2.20 | 0.31 |
| Perpendicular | PLC002477 | 1.71 ± 0.89 | 7.00 ± 0.00 | 11.99 | 2.91 | 5.79 | 0.24 | 0.21 |
| Perpendicular | PLC002477 | 2.59 ± 0.39 | 6.67 ± 1.15 | 17.24 | 4.61 | 12.24 | 0.27 | 0.45 |
| Perpendicular | PLC002317 | 2.36 ± 0.29 | 7.00 ± 1.00 | 16.54 | 3.67 | 13.74 | 0.22 | 0.51 |
| Perpendicular | PLC002319 | 2.99 ± 0.14 | 6.00 ± 0.00 | 17.94 | 4.19 | 9.35 | 0.23 | 0.35 |
| Perpendicular | PLC002477 | 1.37 ± 0.30 | 7.67 ± 0.58 | 10.50 | 7.70 | 10.47 | 0.73 | 0.39 |

FIG. 11

UMBILICAL TISSUE COMPOSITIONS AND METHODS OF USE

CROSS-REFERENCE TO RELATED APPLICATIONS

This application is a continuation application of U.S. application Ser. No. 15/274,100, filed Sep. 23, 2016, which claims the benefit of U.S. Provisional Application No. 62/222,446, filed Sep. 23, 2015, each of which are hereby incorporated herein by reference in their entirety.

BACKGROUND

In placental mammals, the umbilical cord (UC) connects the developing fetus to the placenta. The UC consists of veins and arteries embedded in Wharton's jelly which, in turn, is encased in a layer of amniotic epithelial lining (FIG. 1). The Wharton's jelly and the layer of amniotic epithelial lining comprise the umbilical tissue (UT), while the veins and arteries are the umbilical blood vessels.

The native components of UT include endogenous cells, extracellular matrix (ECM), and bioactive factors. Endogenous cells found in UT include amniotic epithelial cells and stromal cells in Wharton's jelly, such as neonatal fibroblasts, myofibroblasts, mesenchymal stem cells, and macrophages. The ECM of UT is largely made up of collagen, mucopolysaccharides (hyaluronic acid (HA) and chondroitin sulfate). Bioactive factors consist of, but are not limited to, growth factors, cytokines, and anti-microbial peptides. The native components of UT, including endogenous cells, ECM, and bioactive factors, are known to be beneficial for tissue repair and reconstruction. Therefore, there is a need to develop an UT product that removes all immunogenic components (the umbilical blood vessels) of the UC and preserves all of the components of UT.

UT cells (amniotic epithelial cells and Wharton's jelly cells) are known to have therapeutic potentials—they can secrete additional bioactive factors and ECM proteins; they can engraft in local tissues; and they can differentiate into other cells types. A process that keeps UT cells alive and is able to cryopreserve a large area of a relatively thick tissue (>1 mm in thickness) without sacrificing the cell viability is needed.

BRIEF SUMMARY

Disclosed are compositions comprising umbilical tissue, wherein the umbilical tissue comprises one or more engineered channels.

Disclosed are compositions comprising umbilical tissue, wherein the umbilical tissue comprises one or more engineered channels, wherein the umbilical tissue is cryopreserved. Disclosed are compositions comprising umbilical tissue, wherein the umbilical tissue comprises one or more engineered channels, wherein the umbilical tissue is previously cryopreserved.

Disclosed are compositions comprising umbilical tissue, wherein the umbilical tissue comprises one or more engineered channels, wherein the composition is devoid of viable blood cells.

Disclosed are compositions comprising umbilical tissue, wherein the umbilical tissue comprises one or more engineered channels, wherein the composition is devoid of blood vessels.

Disclosed are compositions comprising umbilical tissue, wherein the umbilical tissue comprises one or more engineered channels, wherein the umbilical tissue comprises viable cells native to the umbilical tissue. In some instances, the viable cells comprise mesenchymal stem cells, fibroblasts, epithelial cells, or a combination thereof.

Disclosed are compositions comprising umbilical tissue, wherein the umbilical tissue comprises one or more engineered channels, wherein the umbilical tissue comprises one or more growth factors native to the umbilical tissue. In some instances, the growth factors can be epidermal growth factor (EGF), human growth factor (HGF), keratinocyte growth factor (KGF), basic fibroblast growth factor (bFGF), TGF-β1, 2, and 3, insulin-like growth factor-1 (IGF-1), vascular endothelial growth factor (VEGF), VEGF-C, VEGF-D, TGF-α, Interleukin 10 (IL-10), Interleukin—1 receptor α (IL-1rα), Stromal cell-derived factor-1 (SDF-1), Basic fibroblasts growth factor (bFGF), Neutrophil gelatinase-associated lipocalin (N-Gal), Matrix metalloproteinase 8 (MMP8), Tissue inhibitor of metalloproteinase 1 (TIMP1), TIMP2, Angiopoietin 2 (hAng2), thrombospondin 2 (TSP2), Platelet derived growth factor AA (PDGF-AA), PDGF-AB, Placental growth factor (PIGF), Insulin-like growth factor (IGFBP1), IGFBP2, IGFBP3, α2-macroglobulin, Adiponectin (hACRP30), or Fibronectin.

Disclosed are compositions comprising umbilical tissue, wherein the umbilical tissue comprises one or more engineered channels, wherein the umbilical tissue further comprises one or more cytokines native to the umbilical tissue. In some instances, the one or more cytokines can be stromal cell derived factor-1 (SDF-1 or CXCL12), IL-10, or IL-1rα.

Disclosed are compositions comprising umbilical tissue, wherein the umbilical tissue comprises one or more engineered channels, wherein the umbilical tissue comprises native viable cells. In one aspect, the umbilical tissue comprises at least 70% of native viable cells.

Disclosed are compositions comprising umbilical tissue, wherein the umbilical tissue comprises one or more engineered channels, wherein the umbilical tissue has a Wharton's jelly layer side and an amniotic epithelial layer side, wherein the engineered channels are present on the Wharton's jelly layer side and do not extend through the amniotic epithelial layer side. In some instances, the engineered channels extend through the entire umbilical tissue.

Disclosed are compositions comprising umbilical tissue, wherein the umbilical tissue comprises one or more engineered channels, wherein the composition is devoid of viable immunogenic cells.

Disclosed are compositions comprising umbilical tissue, wherein the umbilical tissue comprises one or more engineered channels further comprising a cryopreservation solution.

Disclosed are compositions comprising umbilical tissue, wherein the umbilical tissue comprises one or more engineered channels, wherein each engineered channel has a diameter ranging from about 0.02 mm to about 2 mm.

Disclosed are compositions comprising umbilical tissue, wherein the umbilical tissue comprises one or more engineered channels, wherein each engineered channel has a longitudinal axis, and wherein each engineered channel has a consistent diameter throughout the entire longitudinal length of the engineered channel.

Disclosed are compositions comprising umbilical tissue, wherein the umbilical tissue comprises one or more engineered channels, wherein each engineered channel has a diameter, and wherein the diameter of at least one engineered channel is equal to the diameter of at least one other engineered channel. In some instances, the engineered channels all have substantially the same diameter.

Disclosed are compositions comprising umbilical tissue, wherein the umbilical tissue comprises one or more engineered channels, wherein each engineered channel has a longitudinal axis and a longitudinal length, and wherein at least one engineered channel has a diameter that varies along the longitudinal length of the engineered channel.

Disclosed are compositions comprising umbilical tissue, wherein the umbilical tissue comprises one or more engineered channels, wherein each engineered channel has a longitudinal axis and a longitudinal length, and wherein each engineered channel has a longitudinal length ranging from about 0.7 mm to about 3.5 mm.

Disclosed are compositions comprising umbilical tissue, wherein the umbilical tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels all have substantially the same longitudinal length.

Disclosed are compositions comprising umbilical tissue, wherein the umbilical tissue comprises one or more engineered channels, wherein the umbilical tissue is capable of releasing umbilical tissue factors at an increased rate over time compared to native umbilical tissue. In some instances the umbilical tissue factors can be angiogenic factors.

Disclosed are compositions comprising umbilical tissue, wherein the umbilical tissue comprises one or more engineered channels, wherein the umbilical tissue is between 1 $cm^2$ and 350 $cm^2$.

Also disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells. In some instances, the viable cells comprise mesenchymal stem cells, fibroblasts, epithelial cells, or a combination thereof.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the growth factors are selected from TGF-β1, TGF-β3, EGF, HGF, KGF, bFGF, and VEGF.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells and further comprising one or more cytokines native to the umbilical cord. In some instances, the one or more cytokines are selected from sdf-1, IL-10, and IL-1rα.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the umbilical tissue has a Wharton's jelly layer side and an amniotic epithelial layer side, wherein the engineered channels are present on the Wharton's jelly layer side and do not extend through the amniotic epithelial layer side.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the umbilical tissue comprises one or more engineered channels. In some instances, the engineered channels extend through the entire umbilical tissue. In some instances, each engineered channel has a diameter ranging from about 0.02 mm to about 2 mm. In some instances, each engineered channel has a longitudinal axis, and wherein each engineered channel has a consistent diameter throughout the entire longitudinal length of the engineered channel. In some instances, each engineered channel has a diameter, and wherein the diameter of at least one engineered channel is equal to the diameter of at least one other engineered channel. In some instances, the engineered channels all have substantially the same diameter.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis, and wherein at least one engineered channel has a diameter that varies along the longitudinal length of the engineered channel.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis, and wherein each engineered channel has a longitudinal length ranging from about 0.7 mm to about 3.5 mm.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels all have substantially the same longitudinal length.

Disclosed are compositions comprising a previously cryopreserved umbilical tissue, wherein after cryopreservation and subsequent thawing the umbilical tissue comprises: a) viable cells native to the umbilical tissue; b) tissue integrity of native umbilical tissue; c) one or more growth factors that are native to the umbilical tissue; and d) depleted amounts of one or more types of functional immunogenic cells, wherein the composition is devoid of blood vessels.

Also disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells. In some instances, the viable cells comprise mesenchymal stem cells, fibroblasts, epithelial cells, or a combination thereof.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the growth factors are selected from TGF-β1, TGF-β3, EGF, HGF, KGF, bFGF, and VEGF.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells and further comprising one or more cytokines native to the umbilical cord. In some instances, the one or more cytokines are selected from sdf-1, IL-10, and IL-1rα.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue has a Wharton's jelly layer side and an amniotic epithelial layer side, wherein the engineered channels are present on the Wharton's jelly layer side and do not extend through the amniotic epithelial layer side.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels. In some instances, the engineered channels extend through the entire umbilical tissue. In some instances, each engineered channel has a diameter ranging from about 0.02 mm to about 2 mm. In some instances, each engineered channel has a longitudinal axis, and wherein each engineered channel has a consistent diameter throughout the entire longitudinal length of the engineered channel. In some instances, each engineered channel has a diameter, and wherein the diameter of at least one engineered channel is equal to the diameter of at least one other engineered channel. In some instances, the engineered channels all have substantially the same diameter.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis, and wherein at least one engineered channel has a diameter that varies along the longitudinal length of the engineered channel.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis, and wherein each engineered channel has a longitudinal length ranging from about 0.7 mm to about 3.5 mm.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels all have substantially the same longitudinal length.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the composition is devoid of blood vessels.

Also disclosed are methods of producing the compositions as described herein, wherein said methods comprise umbilical tissue, comprising forming engineered channels in the umbilical tissue.

Disclosed are methods of producing the compositions comprising umbilical tissue described herein, comprising forming engineered channels in the umbilical tissue, and further comprising treating the umbilical tissue with at least one antibiotic. In some instances, the treating with at least one antibiotic comprises incubating the umbilical tissue with an antibiotic cocktail solution for 18 to 96 hours.

Disclosed are methods of producing the compositions comprising umbilical tissue described herein, comprising forming engineered channels in the umbilical tissue, and further comprising cutting the umbilical tissue to a desired size. In some instances, cutting the umbilical tissue to a desired size comprises placing a cutter onto the umbilical tissue; and cutting the umbilical tissue to maintain a square shape.

Disclosed are methods of producing the compositions comprising umbilical tissue described herein, comprising forming engineered channels in the umbilical tissue, further comprising inspecting the umbilical tissue for excess strings of tissue and discoloration.

Disclosed are methods of producing the compositions comprising umbilical tissue described herein, comprising forming engineered channels in the umbilical tissue, further comprising removing any remaining umbilical cord blood.

Disclosed herein are also methods of treating damaged tissue using the compositions disclosed herein. For example, disclosed are methods of treating damaged tissue comprising administering to the site of the damaged tissue a composition comprising umbilical tissue, wherein the umbilical tissue comprises one or more engineered channels. In some instances, the damaged tissue is from soft tissue damage (muscle, ligament, and tendon), surgical wounds, pelvic floor protrusions, vaginal defects, foot and ankle wounds, chronic wounds, tears or tendon ruptures, nerve damage, or skin wounds.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 9 is a table showing the suture retention raw data.

FIG. 10 is a table showing the biaxial tension testing results; *reported as Mean±StDev.

FIG. 11 is a table showing the uniaxial tension testing results; *reported as Mean±StDev.

DETAILED DESCRIPTION

Figure 1:
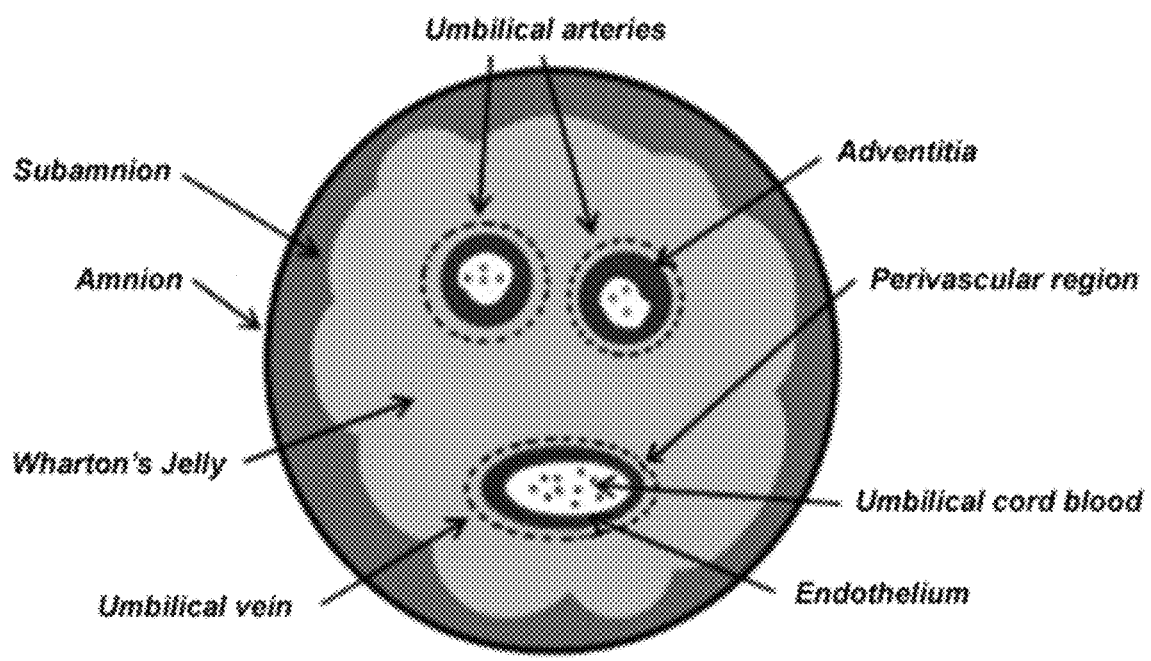
FIG. 1 shows the cross section of an umbilical cord containing two umbilical arteries and a single umbilical vein embedded in mucous connective tissue (Wharton's* jelly), which is covered by an amniotic epithelial lining.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an engineered channel" includes a plurality of such channels, reference to "the engineered channel" is a reference to one or more engineered channels and equivalents thereof known to those skilled in the art, and so forth.

The term "blood vessel" refers to a tubular structure that can carry or transport blood through tissue and organs. For example, the term "blood vessels" can refer to veins, arteries and capillaries.

The term "blood cells" refers to cells of hematopoietic origin. Blood cells can be located in the blood or any tissue.

The term "cytokine" refers to a broad category of molecules (disregarding of its structure) secreted by cells that can affect the behavior of other cells and/or themselves.

The phrase "devoid of viable blood cells" means comprising <10% viable blood cells.

The phrase "devoid of viable immunogenic cells" means comprising <10% viable immunogenic cells. Immunogenic cells can be, but are not limited to, macrophages, T cells, B cells, natural killer cells, and red blood cells.

The term "damaged tissue" refers to tissue that has been impaired or altered in such a way to alter the tissue's normal structure and/or function. For example, damaged tissue can be, but is not limited to soft tissue damage (muscle, ligament, and tendon), surgical wounds, pelvic floor protrusions, vaginal defects, foot and ankle wounds, chronic wounds, tears or tendon ruptures, nerve damage, and skin wounds.

The term "manipulate," "manipulating," or "manipulated" refers to altering or modifying. For example, manipulating umbilical tissue can refer to, but is not limited to, rolling, cutting, shaping, smoothing or flattening of the umbilical tissue, adding engineered channels to the umbilical tissue, or a combination thereof. In some instances, manipulating umbilical tissue can include any alteration to the native umbilical cord that results in the release of growth factors.

The term "native cells" refers to cells that have not been removed or isolated from their original source. For example, umbilical tissue that comprises native viable cells refers to umbilical tissue that has viable cells that were originally present in the umbilical tissue and have not been removed from the umbilical tissue. Cells that have been isolated from umbilical tissue and then later placed back into the umbilical tissue are not considered native cells.

"Engineered channel" as used herein refers to a non-naturally occurring, man-made channel. "Engineered channels" do not include tears or fissures that occur naturally from normal wear and tear of umbilical tissue. Optionally, engineered channels can be mechanically formed or produced. Engineered channels can be formed or produced by other means, including, for example and without limitation, lasers. In exemplary aspects, engineered channels can be formed by mechanical displacement of umbilical tissue. In other exemplary aspects, engineered channels can be formed by mechanical removal of umbilical tissue. In some instances, engineered channels are not chemically produced. Optionally, in exemplary aspects, engineered channels can comprise a primary engineered channel and at least one secondary engineered channel that branches out from and is positioned in fluid communication with the primary channel. In some aspects, it is contemplated that the longitudinal axis of each secondary engineered channel can be positioned at a selected angle relative to the longitudinal axis of the primary engineered channel. It is contemplated that two or more secondary channels can branch out from a primary engineered channel in any desired angular configuration, such as, for example and without limitation, a Y-shaped junction, a T-shaped junction, and the like. However, in other aspects, it is contemplated that at least one secondary engineered channel can have a longitudinal axis that is substantially parallel to and/or positioned in substantial alignment with the longitudinal axis of the primary engineered channel. In some exemplary aspects, engineered channels can extend substantially linearly; however, it is contemplated that engineered channels can also have a curved or arcuate profile if desired. As further disclosed herein, engineered channels can extend from the exterior surface of the Wharton's jelly layer side of an umbilical tissue; however, it is contemplated that engineered channels can begin and extend from any exterior surface of the umbilical tissue. Optionally, in exemplary aspects, when engineered channels extend from multiple surfaces of the umbilical tissue, it is contemplated that at least one engineered channel that extends from a first exterior surface of the umbilical tissue can intersect with at least one other engineered channel that extends from a second exterior surface different than the first exterior surface of the umbilical tissue. Engineered channels can be produced in a controlled or specific manner. In some instances, engineered channels can be considered to be formed in a predictable manner, with a predictable and/or predetermined shape and configuration. Thus, in exemplary aspects, when a plurality of engineered channels are formed as disclosed herein, it is contemplated that at least a portion of the engineered channels can be substantially uniform in appearance. As used herein, a first engineered channel is "substantially uniform" to a second engineered channel when the longitudinal length of the first engineered channel is within 20% (above or below) of the longitudinal length of the second engineered channel. Optionally, it is contemplated that substantially uniform engineered channels can also have substantially the same diameter (maximum cross-sectional dimension), cross-sectional shape, taper profile, and the like. Optionally, in exemplary aspects, when a plurality of engineered channels are formed as disclosed herein, at least 20% of the engineered channels can be substantially uniform, with at least 20% of the engineered channels having respective longitudinal lengths that fall within 20% of the longitudinal length of a first engineered channel. In further exemplary aspects, at least 30%, at least 40%, at least 50%, at least 60%, at least 70%, at least 80%, or at least 90% of the engineered channels can be substantially uniform. Optionally, in further exemplary aspects, the longitudinal axes of at least a portion of the engineered channels can be substantially parallel to one another. For example, in these aspects, it is contemplated that the longitudinal axes of at least 20% of the engineered channels can be substantially parallel to one another. In further exemplary aspects, at least 30%, at least 40%, at least 50%, at least 60%, at least 70%, at least 80%, or at least 90% of the engineered channels can be substantially parallel to one another. In still further exemplary aspects, the longitudinal axes of substantially uniform engineered channels as disclosed herein can optionally be substantially parallel to one another. However, it is contemplated that engineered channels can be substantially uniform without being parallel to one another.

The phrase "substantially equal to the longitudinal length" refers to the longitudinal length of at least one engineered channel being within 10, 20, 30, 40, 50, 60, 70, 80, 90, or 100% of the longitudinal length of a second engineered channel. In some instances, the longitudinal length of at least one engineered channel is within 50% or greater of the longitudinal length of a second engineered channel.

The phrase "substantially the same diameter" refers to the diameters of two or more engineered channels having diameters 10, 20, 30, 40, 50, 60, 70, 80, 90, or 100% of each other.

The phrase "substantially the same longitudinal length" refers to the longitudinal length of two or more engineered channels having longitudinal lengths 10, 20, 30, 40, 50, 60, 70, 80, 90, or 100% of each other.

The phrase "substantially linearly" refers to the at least 10, 20, 30, 40, 50, 60, 70, 80, 90, or 100% of the longitudinal length of an engineered channel being linear.

The phrase "substantially parallel" refers to two or more engineered channels being parallel for at least 10, 20, 30, 40, 50, 60, 70, 80, 90, or 100% of their longitudinal axis or longitudinal length.

The term "umbilical tissue" refers to the tissue present in the umbilical cord devoid of any vessel structure. Umbilical tissue is a rich source of mesenchymal stem cells (MSCs). Umbilical tissue comprises a Wharton's jelly layer (mesodermal connective tissue) and an amniotic epithelial layer.

The term "umbilical tissue factors" refers to any factor that originates from umbilical tissue. Examples of umbilical tissue factors can be, but are not limited to, growth factors, cytokines, antimicrobial peptides, proteases and their inhibitors.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

"Subject" as used herein refers to a living individual with damaged tissue. The term "subject" includes domesticated animals (e.g., cats, dogs, etc.), livestock (e.g., cattle, horses, pigs, sheep, goats, etc.), and laboratory animals (e.g., mouse, rabbit, rat, guinea pig, etc.). In one aspect, a subject is a mammal. In another aspect, a subject is a human. The term does not denote a particular age or sex. Thus, adult, child, adolescent and newborn subjects, whether male or female, are intended to be covered.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Compositions Comprising Umbilical Tissue

Disclosed are compositions comprising umbilical tissue, wherein the umbilical tissue comprises one or more engineered channels.

Disclosed are compositions comprising umbilical tissue, wherein the umbilical tissue comprises one or more engineered channels, wherein the umbilical tissue is cryopreserved. Also disclosed are compositions comprising umbilical tissue, wherein the umbilical tissue comprises one or more engineered channels, wherein the umbilical tissue is previously cryopreserved. Previously cryopreserved umbilical tissue refers to umbilical tissue that has been cryopreserved and since removed from cryopreservation. In some instances, removed from cryopreservation means the umbilical tissue has been removed from a cryopreservation solution. In some instances, removed from cryopreservation means the umbilical tissue has been thawed after cryopreservation.

Disclosed are compositions comprising umbilical tissue, wherein the umbilical tissue comprises one or more engineered channels, wherein the composition is devoid of viable blood cells. In some instances, one or more anticoagulants can be used to help remove blood and blood products, for instance ACD-A (anticoagulant Citrate dextrose solution, solution A, USP), heparin, dalteparin sodium, and bivalirudin.

Disclosed are compositions comprising umbilical tissue, wherein the umbilical tissue comprises one or more engineered channels, wherein the composition is devoid of blood vessels. In some instances, the disclosed compositions are devoid of the two arteries and one vein typically found in the umbilical tissue.

Disclosed are compositions comprising umbilical tissue, wherein the umbilical tissue comprises one or more engineered channels, and wherein the umbilical tissue comprises viable cells native to the umbilical tissue. Cells native to the umbilical tissue refers to cells that are present in naturally occurring umbilical tissue. In some instances, the viable cells can be mesenchymal stem cells, fibroblasts, epithelial cells, or a combination thereof.

Disclosed are compositions comprising umbilical tissue, wherein the umbilical tissue comprises one or more engineered channels, and wherein the umbilical tissue comprises one or more growth factors native to the umbilical tissue. Growth factors native to the umbilical tissue refer to growth factors that are present in naturally occurring umbilical tissue. In some instances, the growth factors can be epidermal growth factor (EGF), human growth factor (HGF), keratinocyte growth factor (KGF), basic fibroblast growth factor (bFGF), TGF-β1, 2, and 3, insulin-like growth factor-1 (IGF-1), vascular endothelial growth factor (VEGF), VEGF-C, VEGF-D, TGF-α, Interleukin 10 (IL-10), Interleukin—1 receptor α (IL-1rα), Stromal cell-derived factor-1 (SDF-1), Basic fibroblasts growth factor (bFGF), Neutrophil gelatinase-associated lipocalin (N-Gal), Matrix metalloproteinase 8 (MMP8), Tissue inhibitor of metalloproteinase 1 (TIMP1), TIMP2, Angiopoietin 2 (hAng2), thrombospondin 2 (TSP2), Platelet derived growth factor AA (PDGF-AA), PDGF-AB, Placental growth factor (PIGF), Insulin-like growth factor (IGFBP1), IGFBP2, IGFBP3, α2-macroglobulin, Adiponectin (hACRP30), or Fibronectin.

Disclosed are compositions comprising umbilical tissue, wherein the umbilical tissue comprises one or more engineered channels, wherein the umbilical tissue further comprises one or more cytokines native to the umbilical tissue. Cytokines native to the umbilical tissue refers to cytokines that are present in naturally occurring umbilical tissue. In some instances, the one or more cytokines can be stromal cell derived factor-1 (sdf-1 or CXCL12), IL-10, or IL-1rα. Disclosed are compositions comprising umbilical tissue, wherein the umbilical tissue comprises one or more engineered channels, wherein the umbilical tissue comprises native viable cells. Also disclosed are compositions comprising umbilical tissue, wherein the umbilical tissue comprises one or more engineered channels, wherein the umbilical tissue comprises at least 70% native viable cells. Disclosed are compositions comprising umbilical tissue, wherein the umbilical tissue comprises one or more engineered channels, wherein the umbilical tissue comprises at least 5%, 10%, 15%, 20%, 25%, 30%, 35%, 40%, 45%, 50%, 55%, 60%, 65%, 70%, 75%, 80%, 85%, 90% or 95% native viable cells. Umbilical tissue comprising at least 70% native viable cells means that there are at least 70% native viable cells in the umbilical tissue compared to the number of viable cells in the umbilical tissue prior to processing. For example, the umbilical tissue prior to processing can have 10%, 20%, 30%, 40%, 50%, 60%, 70%, 80%, 90%, or 100% of viable cells from native umbilical cord. Thus, the disclosed compositions comprising at least 70% native viable cells means that the compositions comprise 70% of viable cells from the umbilical tissue prior to processing and not necessarily 70% of viable cells compared to native umbilical tissue. In an aspect, the native viable cells are cells that are native to the original umbilical cord tissue (e.g. the umbilical cord tissue used in the methods described herein) and have not been removed from the tissue. For example, native viable cells are not cells that have been seeded on the umbilical tissue from the same or a different source.

Disclosed are compositions comprising umbilical tissue, wherein the umbilical tissue comprises one or more engineered channels, wherein the umbilical tissue has a Wharton's jelly layer side and an amniotic epithelial layer side, wherein the engineered channels are present on the Wharton's jelly layer side.

Disclosed are compositions comprising umbilical tissue, wherein the umbilical tissue comprises one or more engineered channels, wherein the umbilical tissue has a Wharton's jelly layer side and an amniotic epithelial layer side, wherein the engineered channels are present on the Wharton's jelly layer side and do not extend through the amniotic epithelial layer side.

Disclosed are compositions comprising umbilical tissue, wherein the umbilical tissue comprises one or more engineered channels, wherein the umbilical tissue has a Wharton's jelly layer side and an amniotic epithelial layer side, wherein the engineered channels are present on the Wharton's jelly layer side and extend through the entire umbilical tissue.

Disclosed are compositions comprising umbilical tissue, wherein the umbilical tissue comprises one or more engineered channels, wherein the composition is devoid of viable immunogenic cells.

Disclosed are compositions comprising umbilical tissue, wherein the umbilical tissue comprises one or more engineered channels and further comprising a cryopreservation solution. The cryopreservation solution can comprise DMSO, HSA, physiological saline solution, or a combination thereof. In some instances, the cryopreservation solution comprises 5%, 10%, 15%, 20%, 25%, 30%, 35%, 40%, 45%, 50%, 55%, 60%, 65%, 70%, 75%, 80%, 85%, 90%, 95%, or 100% DMSO. In some instances, the cryopreservation solution comprises 5% or less, 10% or less, 15% or less, 20% or less, 25% or less, 30% or less, 35% or less, 40% or less, 45% or less, or 50% or less HSA.

Disclosed are compositions comprising umbilical tissue, wherein the umbilical tissue comprises one or more engineered channels, wherein each engineered channel has a diameter ranging from about 0.02 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels can be large enough for at least one cell to fit inside the engineered channel. The average size of most mammalian cells is 10-30 μm, therefore, the diameter of the engineered channels can be larger than 10-30 μm. In some instances, the diameter of the engineered channel can be 8 μm, which can be smaller than the size of a cell but still large enough for a cell to migrate into the engineered channel. In some instances, the diameter of the engineered channels is large enough for multiple cells to fit inside the engineered channel. In some instances, the diameter of the engineered channels is smaller than 10 μm. The engineered channels stimulate the release of growth factors. Growth factors are much smaller than cells and therefore can travel through channels smaller than 10 μm. When determining diameter size, the height of the umbilical tissue should be considered. Engineered channels having diameters too much larger than 2 mm can lead to excessive tissue loss which can lead to weakening of the mechanical structure of the tissue and loss of tissue function.

Disclosed are compositions comprising umbilical tissue, wherein the umbilical tissue comprises one or more engineered channels, wherein the umbilical tissue comprises a Wharton's jelly layer side and a amniotic epithelial layer side, wherein the Wharton's jelly layer side and the amniotic epithelial layer side each comprise an exterior surface, wherein the engineered channels comprise a first end defined in the exterior surface of the Wharton's jelly layer side of the umbilical cord and an opposed second end defined somewhere in the umbilical tissue other than the exterior surface of the Wharton's jelly layer side. In some instances, the second end of the engineered channel is within the umbilical tissue, between the exterior surface of the Wharton's jelly layer side and the exterior surface of the amniotic epithelial layer side. In some instances, the second end of the engineered channel is in the exterior surface of the amniotic epithelial layer side.

Disclosed are compositions comprising umbilical tissue, wherein the umbilical tissue comprises one or more engineered channels, wherein the engineered channels comprise a first end defined in the exterior surface of the Wharton's jelly layer side of the umbilical cord and an opposed second end defined somewhere in the umbilical tissue other than the exterior surface of the Wharton's jelly layer side, and wherein the first ends of the engineered channels are substantially evenly spaced about the exterior surface of the Wharton's jelly layer side of the umbilical tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the umbilical tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the Wharton's jelly layer side of the umbilical tissue. Optionally, in still further exemplary aspects, the first ends of the engineered channels can be spaced apart in a configuration in which the separation distance between the first ends of neighboring channels is selectively varied to thereby produce a desired channel pattern.

Disclosed are compositions comprising umbilical tissue, wherein the umbilical tissue comprises one or more engineered channels, wherein each engineered channel has a longitudinal axis and a longitudinal length. In some instances, each engineered channel has a consistent diameter throughout the entire longitudinal length of the engineered channel. As used herein, the term "diameter" refers to the largest cross-sectional distance defined by the channel, and it is contemplated that the engineered channel can have any desired cross-sectional shape, including, for example and without limitation, a polygonal shape, such as a circle, an ellipse, a square, a rectangle, a rhombus, a trapezoid, and the like. The disclosed compositions can be attached to healthy tissue in a subject to replace damaged tissue. The engineered channels within the umbilical tissue of the composition provide a greater surface area for the umbilical tissue. The greater surface area can allow for growth factors and cells from the subject's healthy tissue to contact the umbilical tissue of the composition in more places and allow for better integration of the umbilical tissue into the subject. The engineered channels also allow growth factors and cells preserved within the umbilical tissue to release from the umbilical tissue and contact the subject. In some instances, the diameter of an engineered channel can vary along the longitudinal length of the engineered channel. For example, the diameter of the engineered channel can get narrower or larger (e.g. cone shaped). In some instances, at least one engineered channel has a diameter that varies along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (i.e., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising umbilical tissue, wherein the umbilical tissue comprises one or more engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e. a first group of channels) can all have substantially the same diameter and another portion of the engineered channels (i.e. a second group of channels) can all have substantially the same diameter wherein the at least two portions of engineered channels do not have the same diameter.

Disclosed are compositions comprising umbilical tissue, wherein the umbilical tissue comprises one or more engineered channels, wherein each engineered channel has a longitudinal axis and a longitudinal length, and wherein each engineered channel has a longitudinal length ranging from about 0.7 mm to about 3.5 mm. In some instances, each engineered channel can have a longitudinal length ranging from about 0.1 mm to about 5 mm. Longitudinal lengths can vary. In some instances, each engineered channel can have a longitudinal length equal to the longitudinal length of the umbilical tissue.

Disclosed are compositions comprising umbilical tissue, wherein the umbilical tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e. a first group of channels) can all have substantially the same longitudinal length and another portion of the engineered channels (i.e. a second group of channels) can all have substantially the same longitudinal length, wherein the at least two portions of engineered channels do not have the same longitudinal length.

Disclosed are compositions comprising umbilical tissue, wherein the umbilical tissue comprises one or more engineered channels, wherein the umbilical tissue is capable of releasing umbilical factors, such as angiogenic factors, at an increased rate over time compared to native umbilical tissue. In some instances, the umbilical tissue releases umbilical factors, such as angiogenic factors, at an increased rate over time compared to native umbilical tissue. In some instances, the angiogenic factors can be growth factors. For example, the disclosed compositions can have 10% greater release of growth factors in comparison to growth factor levels released by native umbilical tissue for the same period of time. In some instances, the growth factor can be EGF, HGF, KGF, bFGF, TGF-β1, 2, and 3, IGF-1, VEGF, VEGF-C, VEGF-D, TGF-α, IL-10, IL-1rα, SDF-1, bFGF, N-Gal, MMP8, TIMP1, TIMP2, hAng2, TSP2, PDGF-AA, PDGF-AB, PlGF, IGFBP1, IGFBP2, IGFBP3, α2-macroglobulin, hACRP30, or Fibronectin.

Disclosed are compositions comprising umbilical tissue, wherein the umbilical tissue comprises one or more engineered channels, wherein the umbilical tissue is between 1 cm$^2$ and 350 cm$^2$. Removing the blood vessels from the umbilical cord allows for larger pieces of umbilical tissue to be used instead of having to cut around the blood vessels.

B. Compositions Comprising Previously Cryopreserved Umbilical Tissue

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells. As referred to herein, "tissue integrity" refers to the tensile strength, yield, and suture pull-out strength of the umbilical tissue. "Tissue integrity" can also refer to the cellular or structural integrity of the tissue.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the viable cells comprise mesenchymal stem cells, fibroblasts, epithelial cells, or a combination thereof.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the growth factors are TGF-β1, TGF-β3, EGF, HGF, KGF, bFGF, or VEGF.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells and further comprising one or more cytokines native to the umbilical cord. Cytokines native to the umbilical tissue refers to cytokines that are present in naturally occurring umbilical tissue. In some instances, the one or more cytokines are sdf-1, IL-10, or IL-1rα.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein the umbilical tissue has a Wharton's jelly layer side and an amniotic epithelial layer side. In some instances, the engineered channels are present on the Wharton's jelly layer side. In some instances, the engineered channels are present on the Wharton's jelly layer side and do not extend through the amniotic epithelial side. In some instances, the engineered channels extend through the entire umbilical tissue.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a diameter ranging from about 0.02 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels is large enough for at least one cell to fit inside the engineered channel. The average size of most mammalian cells is 10-30 μm, therefore, the diameter of the engineered channels can be larger than 10-30 μm. In some instances, the diameter of the engineered channel can be 8 μm, which can be smaller than the size of a cell but still large enough for a cell to squeeze into the engineered channel. In some instances, the diameter of the engineered channels is large enough for multiple cells to fit inside the engineered channel. In some instances, the diameter of the engineered channels is smaller than 10 μm. The engineered channels stimulate the release of growth factors. Growth factors are much smaller than cells and therefore can travel through channels smaller than 10 μm. When determining diameter size, the height of the umbilical tissue should be considered. Engineered channels having diameters too much larger than 2 mm can lead to excessive tissue loss which can lead to weakening of the mechanical structure of the tissue and loss of tissue function.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein the umbilical tissue has a Wharton's jelly layer side and an amniotic epithelial layer side, wherein the Wharton's jelly layer side and the amniotic epithelial layer side each comprise an exterior surface, wherein the engineered channels comprise a first end defined in the exterior surface of the Wharton's jelly layer side of the umbilical cord and an opposed second end defined somewhere in the umbilical tissue other than the exterior surface of the Wharton's jelly layer side. In some instances, the second end of the engineered channel is within the umbilical tissue, between the exterior surface of the Wharton's jelly layer side and the exterior surface of the amniotic epithelial layer side. In some instances, the second end of the engineered channel is in the exterior surface of the amniotic epithelial layer side. In some instances, the first ends of the engineered channels are substantially evenly spaced about the exterior surface of the Wharton's jelly layer side of the umbilical tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the umbilical tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the Wharton's jelly layer side of the umbilical tissue. Optionally, in still further exemplary aspects, the first ends of the engineered channels can be spaced apart in a configuration in which the separation distance between the first ends of neighboring channels is selectively varied to thereby produce a desired channel pattern.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis and a longitudinal length. In some instances, each engineered channel has a consistent diameter throughout the entire longitudinal length of the engineered channel. As used herein, the term "diameter" refers to the largest cross-sectional distance defined by the channel, and it is contemplated that the engineered channel can have any desired cross-sectional shape, including, for example and without limitation, a polygonal shape, such as a circle, an ellipse, a square, a rectangle, a rhombus, a trapezoid, and the like. The disclosed compositions can be attached to healthy tissue in a subject to replace damaged tissue. The engineered channels within the umbilical tissue of the composition provide a greater surface area for the umbilical tissue. The greater surface area can allow for growth factors and cells from the subject's healthy tissue to contact the umbilical tissue of the composition in more places and allow for better integration of the umbilical tissue into the subject. The engineered channels also allow growth factors and cells preserved within the umbilical tissue to release from the umbilical tissue and contact the subject. In some instances, the diameter of an engineered channel can vary along the longitudinal length of the engineered channel. For example, the diameter of the engineered channel can get narrower or larger (e.g. cone shaped). In some instances, at least one engineered channel has a diameter that varies along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (e.g., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e. a first group of channels) can all have substantially the same diameter and another portion of the engineered channels (i.e. a second group of channels) can all have substantially the same diameter wherein the at least two portions of engineered channels do not have the same diameter.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis and a longitudinal length, and wherein each engineered channel has a longitudinal length ranging from about 0.7 mm to about 3.5 mm. In some instances, each engineered channel can have a longitudinal length ranging from about 0.1 mm to about 5 mm. Longitudinal lengths can vary. In some instances, each engineered channel can have a longitudinal length equal to the longitudinal length of the umbilical tissue.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the umbilical tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e. a first group of channels) can all have substantially the same longitudinal length and another portion of the engineered channels (i.e. a second group of channels) can all have substantially the same longitudinal length, wherein the at least two portions of engineered channels do not have the same longitudinal length.

Disclosed are compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells, wherein the composition is devoid of blood vessels. Umbilical tissue often has two arteries and one vein. In some instances, the disclosed compositions are devoid of these two arteries and one vein.

C. Methods of Producing Compositions Comprising Umbilical Tissue

Disclosed are methods of producing the disclosed compositions, comprising forming engineered channels in the umbilical tissue. For example, disclosed are methods of producing compositions comprising umbilical tissue, wherein the method comprises forming engineered channels in the umbilical tissue. Forming engineered channels in the umbilical tissue can be performed by manipulating the umbilical tissue. Manipulating the umbilical tissue can comprise cutting, rolling, shaping, smoothing, or flattening while forming engineered channels in the umbilical tissue. In some instances, manipulating the umbilical tissue comprises flattening the tissue and forming the engineered channels. The rolling or flattening of the umbilical tissue can be performed with a laminating roller, such as a bubble buster, or a microdermal roller. Manipulating the umbilical tissue can result in the elevated release of native growth factors. Flattening of the umbilical tissue can provide a uniform thickness of the final product.

Disclosed are methods of producing compositions comprising umbilical tissue, comprising forming engineered channels in the umbilical tissue, further comprising treating the umbilical tissue with at least one antibiotic. In some instances, treating with at least one antibiotic comprises incubating the umbilical tissue with an antibiotic cocktail solution for 18 to 96 hours. In some instances, the umbilical tissue can be treated with two or more antibiotics simultaneously or consecutively. In some instances, the treatment with at least one antibiotic can be performed prior to cryopreservation. In some instances, the umbilical tissue can be cryopreserved in a solution comprising at least one antibiotic.

Disclosed are methods of producing compositions comprising umbilical tissue, comprising forming engineered channels in the umbilical tissue, and further comprising cutting the umbilical tissue to a desired size. In some instances, cutting the umbilical tissue to a desired size comprises placing a cutter onto the umbilical tissue; and cutting the umbilical tissue to maintain a square shape. A cutter can be any device such as, but not limited to, a stencil that helps cut the tissue. A cutter can hold the tissue in place or provide a specific shape for the tissue to be cut to.

Disclosed are methods of producing compositions comprising umbilical tissue, comprising forming engineered channels in the umbilical tissue, and further comprising inspecting the umbilical tissue for excess strings of tissue and discoloration.

Disclosed are methods of producing compositions comprising umbilical tissue, comprising forming engineered channels in the umbilical tissue, further comprising removing any remaining blood.

D. Methods of Treating Damaged Tissue

Disclosed are methods of treating damaged tissue comprising administering to the site of the damaged tissue any one of the disclosed compositions. For example, disclosed are methods of treating damaged tissue comprising administering to the site of the damaged tissue compositions comprising umbilical tissue, wherein the umbilical tissue comprises one or more engineered channels.

Disclosed are methods of treating damaged tissue comprising administering to the site of the damaged tissue any one of the disclosed compositions, wherein the damaged tissue can be, but is not limited to, soft tissue damage (muscle, ligament, and tendon), surgical wounds, pelvic floor protrusions, vaginal defects, foot and ankle wounds, chronic wounds, tears or tendon ruptures, nerve damage, or skin wounds In some instances, the damaged tissue can be from pelvic organ prolapse, stress urinary incontinence, reformed or denovo adhesions, surgical procedures such as reconstructive surgery, including plastic surgery, and laparoscopic surgery, wounds, ulcers, necrosis, injured soft tissue such as tendons and ligaments.

In some instances, disclosed are methods of repairing tendon damage comprising administering to the damaged tendon any one of the disclosed compositions. For example, disclosed are methods of repairing tendon damage comprising administering to the damaged tendon a composition comprising umbilical tissue, wherein the umbilical tissue comprises one or more engineered channels. Tendon damage can be, but is not limited to, Achilles tendon rupture, Haglund's deformity, Achilles tendonitis/tenosynovitis, bursitis, peroneus brevis tendon damage, talofibular ligament injury, posterior tibial fraying/posterior tibial tendon dysfunction, or a combination thereof.

Disclosed are methods of treating or preventing adhesions comprising administering to an area of adhesion formation or possible adhesion formation any one of the disclosed compositions. For example, disclosed are methods of treating or preventing adhesions comprising administering to an area of adhesion formation or possible adhesion formation a composition comprising umbilical tissue, wherein the umbilical tissue comprises one or more engineered channels.

Disclosed are methods of treating or preventing infection comprising administering to an area of infection or possible infection any one of the disclosed compositions. For example, disclosed are methods of treating or preventing infection comprising administering to an area of infection or possible infection a composition comprising umbilical tissue, wherein the umbilical tissue comprises one or more engineered channels. In some instances, the infection occurs during or post-surgery, such as, but not limited to, abdominal surgery.

E. Kits

The materials described above as well as other materials can be packaged together in any suitable combination as a kit useful for performing, or aiding in the performance of, the disclosed method. It is useful if the kit components in a given kit are designed and adapted for use together in the disclosed method. Disclosed are kits comprising any one of the disclosed compositions. For example disclosed are kits comprising compositions comprising umbilical tissue, wherein the umbilical tissue comprises one or more engineered channels. The kits also can contain compositions comprising a previously cryopreserved umbilical tissue, wherein after cryopreservation and subsequent thawing the umbilical tissue comprises: a) cells native to the umbilical tissue, wherein greater than 40% of the cells are viable; b) tissue integrity of native umbilical tissue; c) one or more growth factors that are native to the umbilical tissue; and d) depleted amounts of one or more types of functional immunogenic cells. Also disclosed are kits comprising compositions comprising umbilical tissue, wherein the umbilical tissue comprises one or more engineered channels, wherein the compositions further comprise a cryopreservation solution.

The disclosed kits can also include a tool for cutting the umbilical tissue to the desired size. Tools for cutting or shaving the umbilical tissue can be, but are not limited to, a scalpel, scissors, knives, blades, biters, punchers, or arthroscopic shavers. For example, the kit can comprise at least one of the disclosed compositions and scalpel.

EXAMPLES

Viable cryopreserved umbilical tissue can be utilized for anti-adhesion barrier and for tissue reconstruction surgical wounds including but not limited to pelvic floor repair, vaginal repair, foot and ankle wounds, chronic wounds, tendon repair, and nerve repair.

A. Example 1

Processing and Packaging of the Viable Cryopreserved Umbilical Tissue (CUT) Product Umbilical cord (UC) was isolated from donor placentas received from tissue banks or other qualified tissue recovery agencies. The tissues were collected according to recovery agency SOPs. A procedure for processing the UC is described below.

The UC was removed from the placenta. The cut was made as close to the placental surface as possible.

Figure 2A:
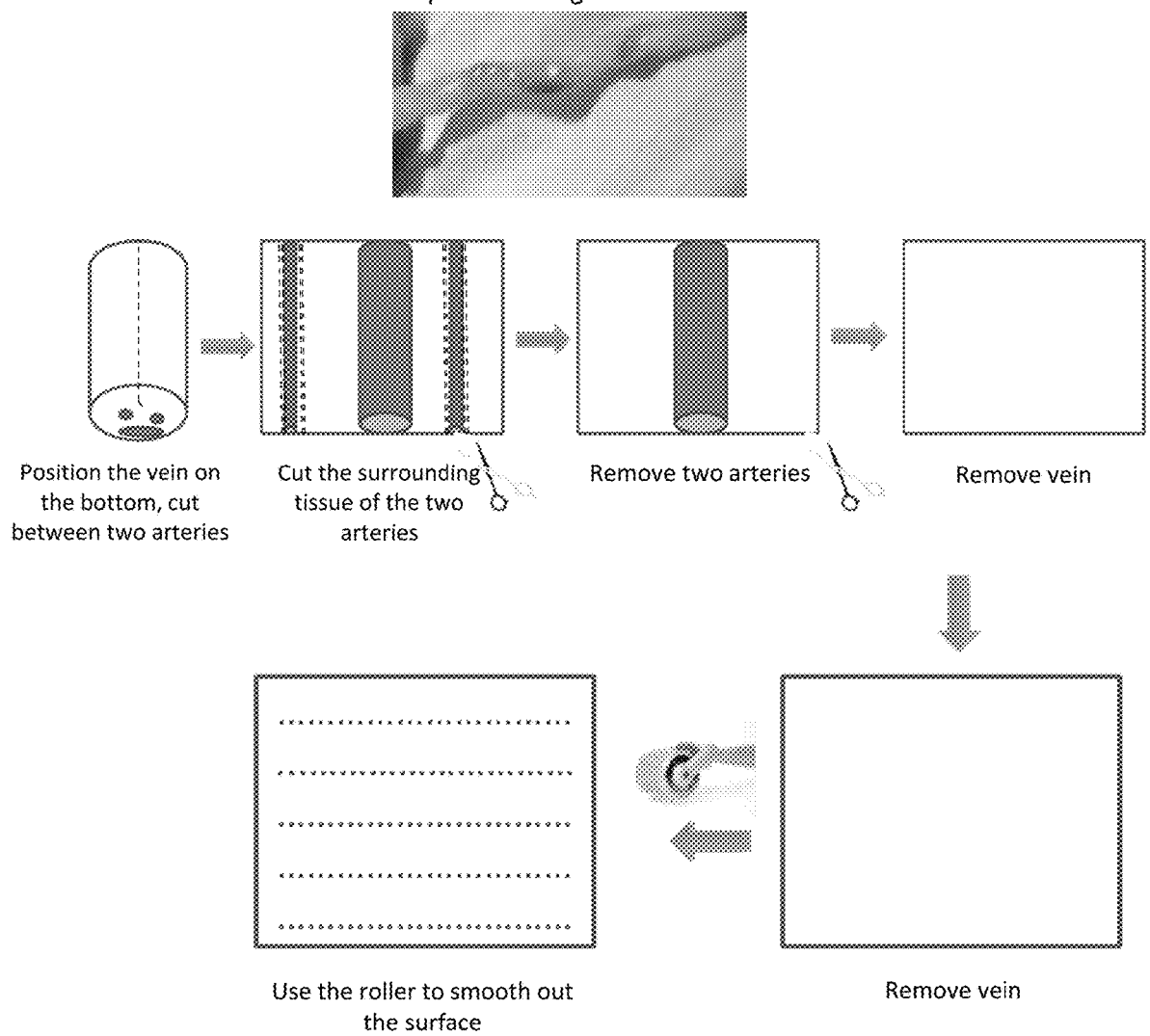
FIG. 2A and FIG. 2B show the schematics of the processing method for straight (A) and coiled (B) umbilical cords. The result is umbilical tissue with engineered channels.

The UC was rinsed with PBS twice to remove any superficial blood clots. Blood vessels were removed for those UCs that are relatively straight (FIG. 2A). The UC was positioned so that the vein is on the bottom, and two arteries are on top. Using a scalpel blade, gentle cuts were made longitudinally in between two arteries and halfway into the depth of the umbilical cord. Care was taken not to section the UC in half.

Using a set of forceps, the arteries were peeled from the surrounding stromal tissue. If arteries are not exposed completely, gentle cuts around the arteries were made using scissors or a scalpel blade.

Blood vessels were removed for those umbilical cords that are coiled. The vein was pierced with a spatula or forceps. With the guidance of the spatula or forceps, the vein was cut open with scissors or a scalpel blade. A scalpel blade was used to cut through the opposite side of the vein with Wharton's Jelly beneath it to expose the arteries. Using a set of forceps, the arteries were peeled from the surrounding stromal tissue.

Figure 2B:
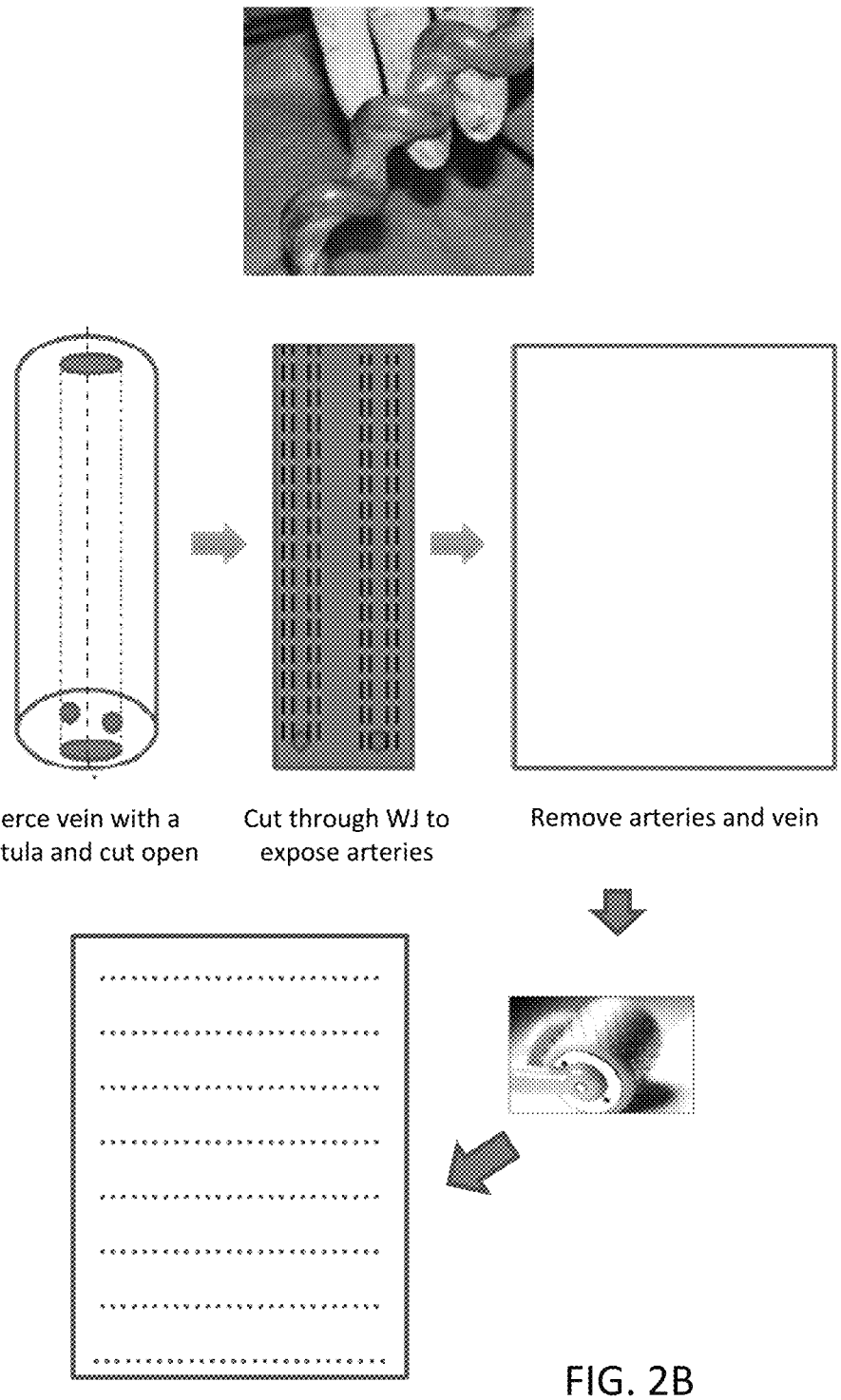

If the UCs are coiled (FIG. 2B), the vein was pierced with a spatula or forceps. With the guidance of the spatula or forceps, the vein was cut open with scissors or a scalpel blade. A scalpel blade was used to cut through the opposite side of the vein with Wharton's Jelly beneath it to expose the arteries. Using a set of forceps, the arteries were peeled from the surrounding stromal tissue After removing the vein and arteries, the UC then becomes umbilical tissue (UT). The UT was rinsed in PBS to remove any residual blood. A laminating roller was used to flatten the umbilical cord. Excess Wharton's Jelly was trimmed off with curved scissors. The steps of flattening and shaping the UT and trimming the Wharton's Jelly can be repeated until the UT surface is smooth. Then the UT was rinsed with PBS twice. Any blood particulates on the tissue were removed.

Antibiotics treatment (optional): Processed UT was incubated in 250 ml Antibiotic Cocktail Solution D for 18 to 84 hours at 37° C., 5% $CO_2$.

Processing units from the UT: The UT was rinsed twice in saline. A scalpel was used to make a perpendicular cut and maintain a squared end. Any excess tissue around the edges of the unit was cut away.

Inspecting the UT for excess strings of tissue and discoloration: Final units of the UT were processed so that extraneous excess strings of tissue or discoloration (signs of blood specs) was not present.

UT units were rinsed twice with saline and cut to desired shape and sizes. Each unit was cryopreserved and were then stored frozen at −80 freezer.

B. Example 2

Assessment of Placental Tissue Cell Viability of the Viable CUT

Trypan Blue exclusion assay: Thawed tissue samples were minced into small cubes and incubated in a warm collagenase II solution (Worthington) for 2.5 hrs. Digested tissue samples were then filtered through a 70-100 µm cell strainer and centrifuged at 2000 rpm to pellet cells released from the tissue. The cell pellets were then resuspended in DMEM containing trypan blue. Cell counting was performed using an automated cell counter, Cellometer.

Live/dead cytotoxicity assay: The Live/dead viability cytotoxicity assay was performed according to manufacture manual (Life Technologies). Briefly, tissue samples were incubated in calcein AM and ethidium homodimer-1 for 30-45 minutes at 37° C. Samples were then washed in PBS and analyzed using fluorescent microscopy. Pictures were taken under 4x. Cell counting was performed using ImageJ (NIH) by two independent operators.

Efficiency of tissue processing and cryopreservation was assessed by % viable cells in the cryopreserved samples versus fresh samples, which was calculated as (viability of cryopreserved tissue post-thaw)/(viability of fresh tissue)× 100%.

Table 1 shows cell viability in fresh and post-thawed umbilical tissue

|  |  | Fresh (% viable cells) | Post-Thaw (% viable cells) | Efficiency of Cryopreservation (%) |
| --- | --- | --- | --- | --- |
| Trypan Blue | PLC002978 | 38.9 | 42.5 | 98.7 |
|  | PLC002895 | 55.3 | 50.5 |  |
|  | mean | 47.1 | 46.5 |  |
| Live/Dead | PLC002853 | 31 | 32 | 95.1% |
|  | PLC002936 | 30 | 27 |  |
|  | BTR151577 | 18 | 16 |  |
|  | mean | 26.3 | 25 |  |

The results shown in Table 1 show the processing method retains >95% of viable cells present in fresh tissues.

C. Example 3

Structural Properties of Viable CUT

Figure 3A:
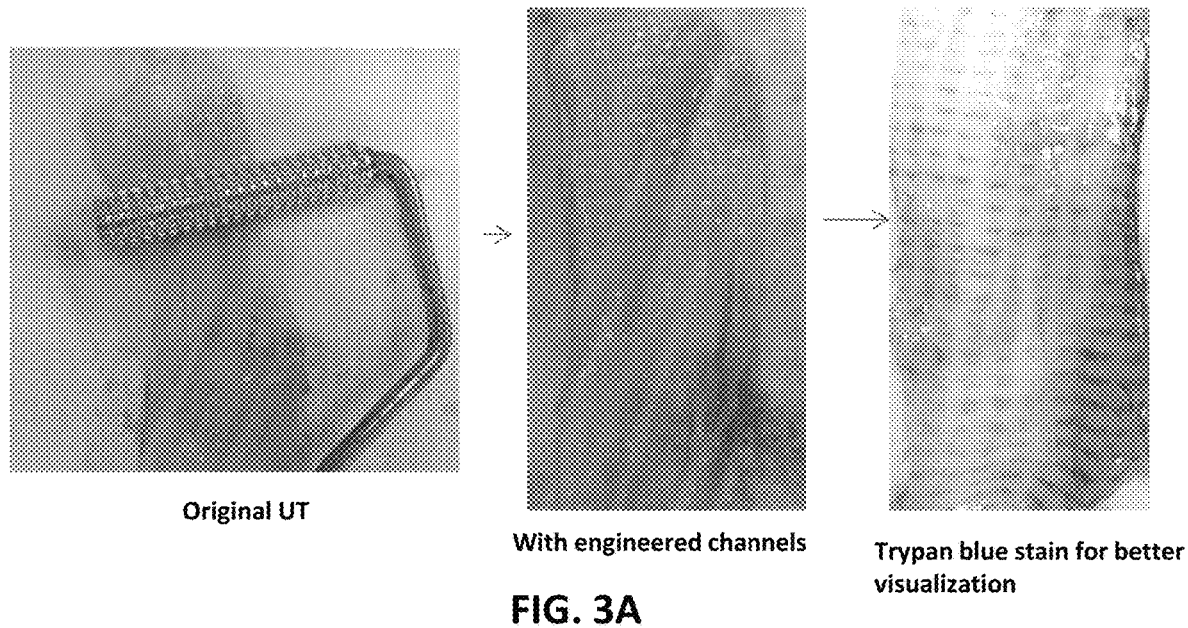
FIG. 3A and FIG. 3B show the structure of umbilical tissue with engineered channels (A) tissue stained with trypan blue to show the channels in the macroscale; (B) histological HA histochemistry of cryopreserved umbilical tissue with and without introducing channels.

To visualize the engineered channel, the roller was stained with trypan blue dye, and the channeling was performed onto UT. FIG. 3A demonstrates trypan blue stained UT with engineered channels clearly shown.

To investigate whether the integrity of the UT was preserved, histological analysis was performed on UT that was either channeled or not channeled. The main ECM protein, hyaluronic acid (HA), was selected for immunochemical staining.

Figure 3B:
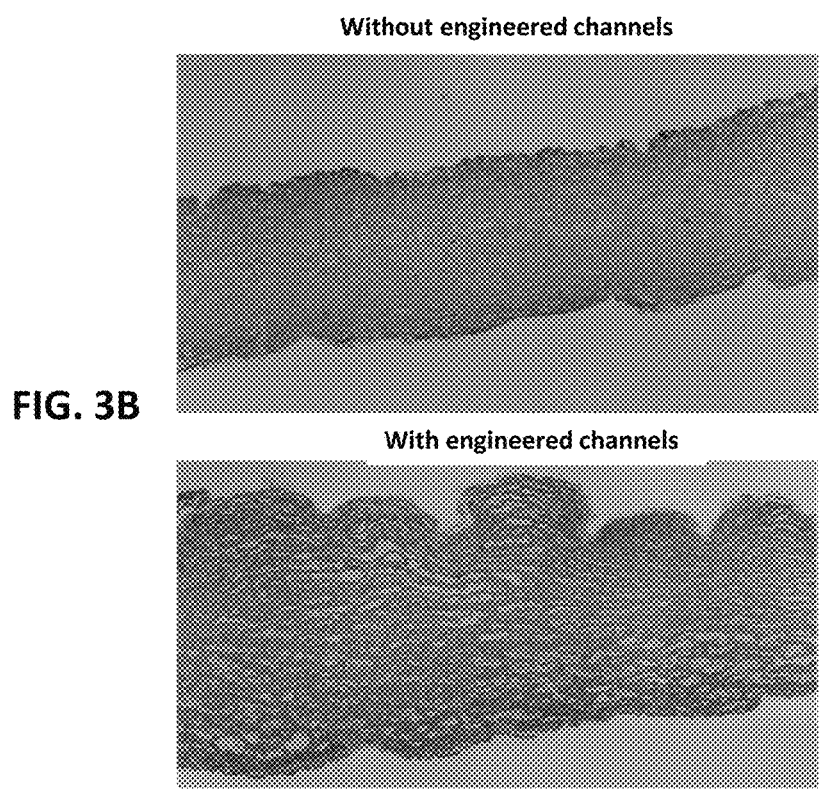

As shown in FIG. 3B, the channeling (processing) created an array of indentation on the umbilical tissue.

D. Example 5

Figure 4:
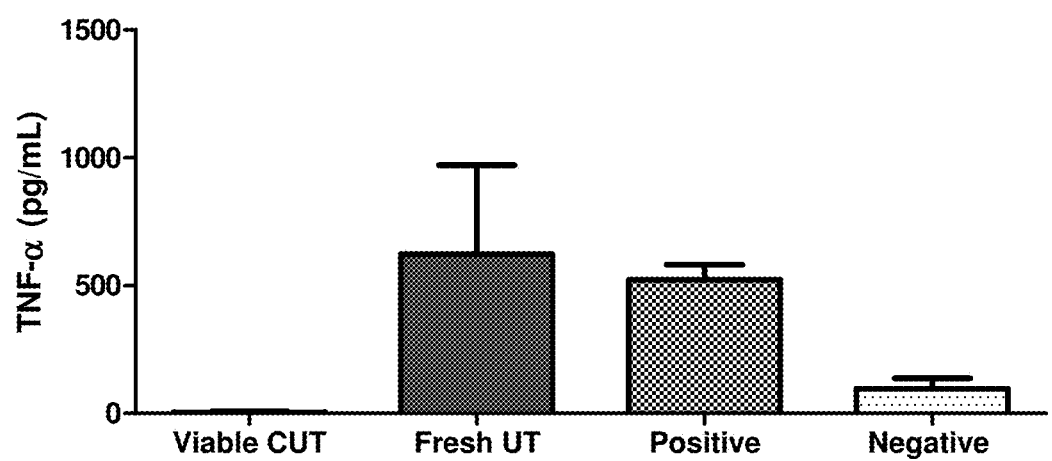
FIG. 4 shows LPS—induced TNF-α release by the cryopreserved umbilical tissue. Human peripheral blood mononuclear cells (hPBMC) that were incubated with and without LPS were served as positive and negative control, respectively.

Immunogenicity of Viable CUT Lipopolysaccharide (LPS)-induced TNF-α secretion assay was performed to determine the immunogenicity of cryopreserved umbilical cord. 2×2 cm pieces of fresh (unprocessed) umbilical tissue and cryopreserved umbilical tissue were incubated with LPS (1 ug/mL) for 24 hours. Human peripheral blood mononuclear cell (hPBMCs) stimulated with and without LPS (1 ug/mL) were considered as positive and negative control, respectively. After 24 hours, supernatants were collected and TNF-α ELISA assay was performed. Results showed that LPS did not activate viable cryopreserved UT to release TNF-α, therefore cryopreserved UT is non-immunogenic (FIG. 4).

E. Example 6

Growth Factor Analysis of Viable CUT

Viable CUT was thawed by directly adding room temperature saline into the straight sided jars. Units were cut into small pieces and then minced using a scalpel into very small cubes (1×1×1 mm) and snap frozen in a homogenization tube placed in a liquid nitrogen bath. Tissue was then homogenized using pre-chilled chamber of the TissueLyser LT (Qiagen) according to the manufacture's recommendations in 1 ml of PBS in the presence of proteinase inhibitor (Roche). Homogenates were then spun down and the supernatants were collected and analyzed for specific growth factors via ELISA

TABLE 2

Growth Factors Present in Viable CUT

| Growth Factor/Cytokine | Range (pg/mL) |
|---|---|
| Transforming growth factor - beta 3 (TGF-β3) | 150-800 |
| TGF-β2 | 593-5942 |
| TGF-β1 | 10000-22000 |
| TGF-α | 7.1-190 |
| Interleukin 10 (IL-10) | 3.9-196 |
| Interleukin - 1 receptor α (IL-1rα) | 3500-27000 |
| Epidermal growth factor (EGF) | 3.7-19 |
| Hepatocyte growth factor (HGF) | 50000-336000 |
| Keratinocytes growth factor (KGF) | 15-298 |
| Stromal cell-derived factor -1 (SDF-1) | 12.5-1270 |
| Basic fibroblasts growth factor (bFGF) | 1287-13226 |
| Vascular endothelial growth factor (VEGF) | 9-36597 |
| VEGF-C | 48-525 |
| VEGF-D | 9-140 |
| Neutrophil gelatinase-associated lipocalin (N-Gal) | 9900-15390 |
| Matrix metalloproteinase 8 (MMP8) | 60-4528 |
| Tissue inhibitor of metalloproteinase 1 (TIMP1) | $1.5 \times 10^6$-$10.6 \times 10^6$ |
| TIMP2 | 22000-35000 |
| Angiopoietin 2 (hAng2) | 21-202 |
| thrombospondin 2 (TSP2) | 94-573 |
| Platelet derived growth factor AA (PDGF-AA) | 6.3-34 |
| PDGF-AB | 3.8-470 |
| Placental growth factor (PlGF) | 700-3000 |
| Insulin-like growth factor (IGFBP1) | 148000-1000000 |
| IGFBP2 | 79000-120000 |
| IGFBP3 | 256000-1000000 |
| α2-macroglobulin | $13 \times 10^6$-$78 \times 10^6$ |
| Adiponectin (hACRP30) | 23000-90000 |
| Fibronectin | 579-17270000 |

F. Example 7

Channeling Increases the Release of Basic FGF (bFGF) and VEGF In Vitro

To demonstrate the effect of channeling on the release of growth factors, viable CUT samples were processed either with or without the channeling step. All other steps including cryopreservation was kept the same for both groups. The units were then thawed and placed in 24-well plates and submerged in 1 mL of low serum culture medium (DMEM+ 1% FBS+2% anti-anti+2% GlutaMAX) and incubated at 37° C. for 1 day, 4 days and 7 days. Conditioned medium was collected at each time point and fresh media was added back to the culture. ELISA was used to analyze the release of key angiogenic growth factor, bFGF and VEGF, overtime.

Figure 5:
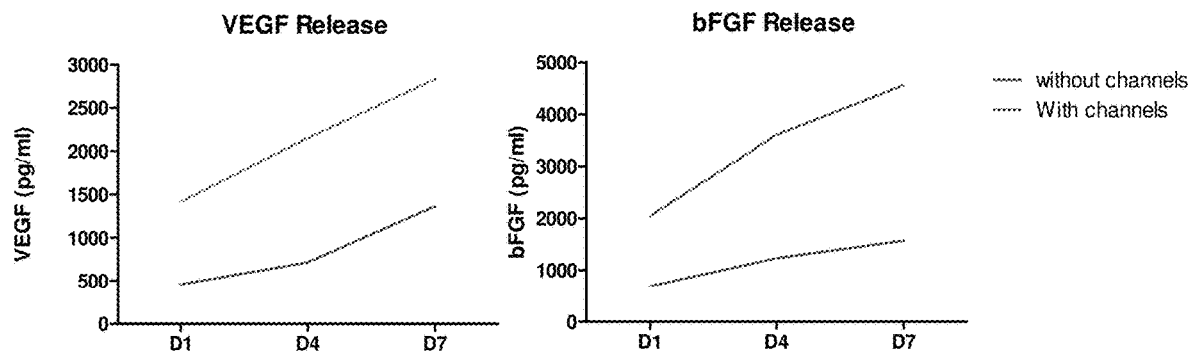
FIG. 5 shows the release of basic FGF and VEGF from cryopreserved umbilical tissue with and without engineered channels over the period of 7 days.

Summary: Channeling of UT increases the release of basic FGF and VEGF from UT tissue, which can promote better integration in vivo (FIG. 5).

G. Example 8

Viable CUT Promotes Cell Attachment In Vitro

To demonstrate the effects of channeling on cell attachment onto viable CUT, human dermal fibroblasts (HDFs) were pre-labeled with calcein-AM and seeded on the top of VCUT for 1 h and 2 h. After the 1 or 2 h incubation, viable CUT was then washed with PBS, and visualized under a fluorescent microscope.

Figure 6:
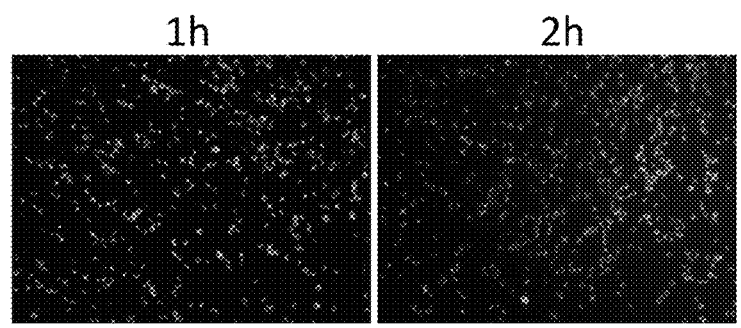
FIG. 6 shows the view of human dermal fibroblasts (HDFs) attached to the viable cryopreserved umbilical tissue.

The results demonstrate that viable CUT promotes HDF attachment (FIG. 6).

H. Example 9

Viable CUT Contains and Releases an Anti-Microbial Peptide, RNase 7

A 2×2 cm cryopreserved umbilical tissue samples was thawed in sterile saline and then incubated in DMEM+1% FBS for 3 days. After 3 days conditioned medium and cell lysates were analyzed for the presence of RNase 7. For tissue lysate preparation tissue pieces were minced and lysed in tissue protein extraction reagent (T-PER) supplemented with proteinase inhibitor (Roche) at room temperature for 40 minutes on a shaker. Insoluble materials were removed by centrifuged at 14,000 rpm for 2 minutes, and resulting tissue lysate was transferred in a new tube. Human RNase 7

ELISA kit (Icosagen) was used to detect the level of RNase 7 in conditioned medium and tissue lysates (Table 3).

TABLE 3

Table showing RNase detection.

|  | Conditioned medium | Tissue lysates |
|---|---|---|
| RNase 7 (pg/mL) | 381-817 | 495-516 |

Results showed that in addition to N-Gal, a protein with antimicrobial properties, viable CUT contains and releases another antimicrobial protein, RNase 7.

I. Example 10

Mechanical Testing on Viable CUT

To characterize the biomechanical properties of viable CUT, the biaxial tension to failure, suture retention and ball burst testing were performed.

Testing samples were obtained from at least 3 different donors and performed in triplicates for each direction (parallel and perpendicular to the vessel direction) for two tests (tension to failure and suture retention). Since the biaxial nature of the ball burst test takes matrix orientation into account, triplicate samples from three samples were used without regard to fiber direction. All specimens were thawed at room temperature, and then thickness was measured through the gage length in an unloaded state using the optical micrometer. A minimum of three thicknesses per specimen was recorded and averaged. To get an accurate thickness measurement the specimens were patted dry to remove excess surface water.

1. Materials and Methods
i. Equipment and Supplies

Materials Testing System (ElectroPuls E3000; Instron); 100 N Load Cell (2530-427; Instron); Pneumatic Wedge Grips (CP101755; Instron); 200 Grit Sandpaper sheets; 220 Grit Sandpaper rings; Optical Micrometer (LS-7030MT; Keyence); Custom ball burst testing fixture (12.5 mm support plate opening w/6.25 mm indenter); Scalpel w/#10 or #11 blades; 0.35 mm diameter steel wire (equivalent to 2-0 suture diameter); 0.9% Sodium Chloride Irrigation USP (B—Braun); Brass square bar stock, 6.25 mm width; Stainless steel ruler (1.0 mm accuracy)

ii. Study Design

Testing specimens were obtained from umbilical tissue samples in each direction (parallel and perpendicular to the primary matrix orientation) for two tests; uniaxial tension and suture retention. Nine (n=9) tissue strips were obtained in the parallel direction from four grafts and nine (n=9) strips were obtained in the perpendicular direction from five grafts for tensile failure testing. Similarly, nine (n=9) specimens were obtained in the parallel direction from four grafts and nine (n=9) specimens were obtained in the perpendicular direction from four grafts for suture retention testing. Since the biaxial nature of the ball burst test takes matrix orientation into account, nine (n=9) specimens from seven grafts were selected without regard to fiber direction.

iii. Specimen Preparation

Specimens were suspended in a cryopreservative solution and shipped frozen on dry ice. The grafts were thawed at room temperature until no ice crystals were present and then placed in 0.9% saline for thickness measurements and biomechanical testing.

iv. Suture Retention Testing

Suture retention specimens (optimal size 2 cm×4 cm) were selected from groups of specimens labeled "2.5 by 5.0 cm" with both parallel and perpendicular oriented grafts. The specimens were clamped in the pneumatic grips with a 2.0 cm tab hanging down from the top clamp. A 25.4 cm long segment of wire was placed through the tab 1.0 cm away from the free end centered in the width of the specimen. The wire was secured to the base of the materials testing system with a custom grip base and post system. The wire was wrapped around a post and twisted around itself in such a way that it would not unwind with the extension of crosshead. The specimen was pulled at a displacement controlled rate of 25.4 mm/sec.

Load and displacement data were recorded by the material testing system's 100N load cell and integrated LVDT position sensor, respectively.

v. Ball Burst Testing

Specimens were selected from the largest grafts provided. Three thickness measurements were obtained in each fiber direction using the laser micrometer and then averaged. Each specimen was then sandwiched between two 220 grit sandpaper rings to prevent slippage during testing and clamped between the plates of the ball burst fixture. Tests were conducted at a displacement rate of 305 mm/min per ASTM Standard D6797-021 (the rate of 25.4 mm/sec (1,524 mm/min) originally proposed was found to be in error and therefore corrected).

Load and displacement data were recorded by the material testing system's 100N load cell and integrated LVDT position sensor, respectively. Displacement was defined as the indenter travel perpendicular to the plane of the umbilical tissue, with zero located on the specimen's top surface. Wall stress was calculated using the formula reported by Freytes et al.2. Stretch is a non-dimensional equivalent of strain in two dimensions2.

vi. Uniaxial Tension Testing to Failure tissue strips were cut using a scalpel and a template consisting of a brass square bar to provide a straight, consistent cutting guide (see FIG. 11 for specimen dimensions). A gage length of 27 mm was set for all specimens, and three thickness measurements within this gage length were obtained using the laser micrometer. Specimen width was measured three times using a ruler and the average was used for calculations. Specimens were placed in the pneumatic grips such that the gage length was the initial distance between grips, with 200 grit sandpaper used between the specimen and grip faces to prevent slippage during testing. Since there were no handling issues, Tyvek was not necessary to facilitate specimen measurement or gripping as originally proposed. All specimens were tested at a displacement controlled rate of 5 mm/sec.

Load and displacement data were recorded by the material testing system's 100N load cell and integrated actuator position sensor, respectively. Maximum stress was calculated as the maximum load divided by the average cross sectional area for each specimen. Strain at maximum stress was the displacement value corresponding to the maximum stress value divided by the gage length. Modulus and stiffness, the linear portions of the stress strain curve and load displacement curves, were taken as the slope of a linear regression of the points on the respective diagram. Values were considered if they were greater than 0.05 mm/mm and less than 80% of the strain at maximum stress. This procedure was repeated consistently for all specimens.

vii. Data Analysis

Descriptive statistics were reported for each of the calculated structural and material properties and include mean, median, standard deviation, ±25th percentile, standard error of the mean (SEM), and normality (Shapiro-Wilk test with $\alpha > 0.05$ indicating normality) analyses.

2. Results

Tissue handling was qualitatively very good. There was no curling over of the edges or excessive sticking to surrounding materials. No difficulties were encountered while cutting specimens to specific sizes.

i. Suture Retention Testing

Figure 7:
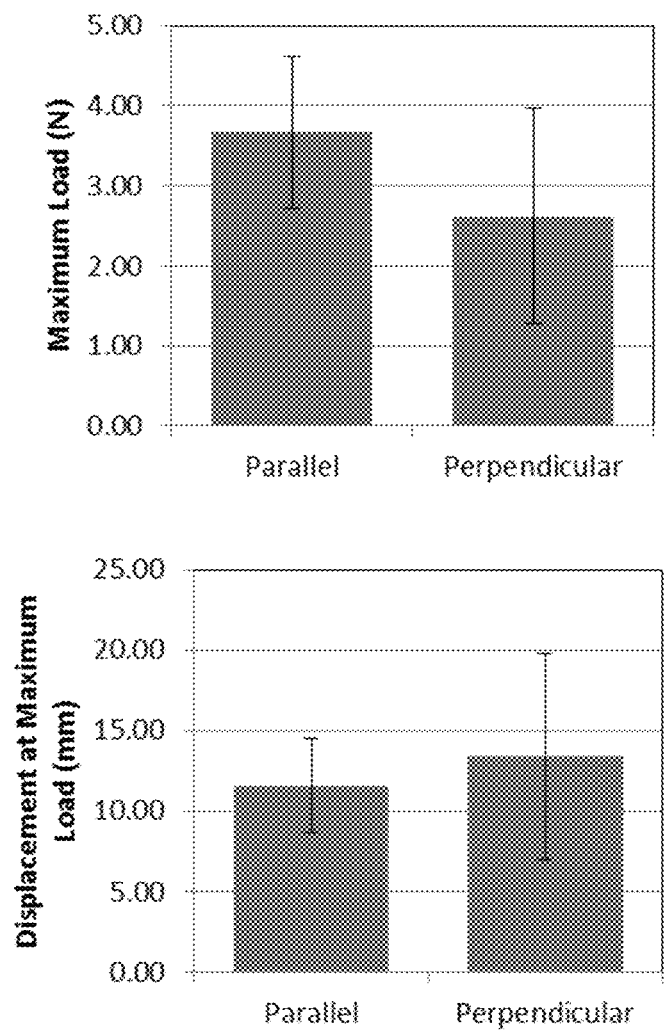
FIG. 7 shows the maximum load (N) and corresponding displacement (mm) of the suture retention test (Mean±StDev).

Load and displacement data are shown in Table 4 and FIG. 7. No slippage at the grips was noticed for any specimen nor was there any unwinding of the wire for any specimen.

TABLE 4

Suture retention testing results

| | Fiber Orientation | | | |
|---|---|---|---|---|
| | Parallel | | Perpendicular | |
| Measured Value | Load | Displacement | Load | Displacement |
| Mean ± StDev | 3.67 ± 0.95 | 11.56 ± 2.93 | 2.62 ± 1.34 | 13.38 ± 6.42 |
| 25th Percentile | 3.26 | 9.13 | 2.98 | 9.26 |
| Median | 3.73 | 12.39 | 1.38 | 15.50 |
| 75th Percentile | 4.12 | 14.04 | 3.26 | 17.86 |
| SEM | 0.32 | 0.98 | 0.45 | 2.14 |
| Normality | Normal | Normal | Normal | Normal | ii. Ball Burst Testing

Data are shown in Table 5. There were no observed failures near the support rim of the ball burst stand. All of the failures occurred in the vicinity of the tip of the indenter. All specimens were securely gripped during testing with no observed slippage around the edge of the plate opening.

TABLE 5

Biaxial tension testing results.

| | Maximum Load (N) | Displacement at Maximum Load (mm) | Maximum Wall Stress (MPa) | Stretch at Maximum Load (mm/mm) |
|---|---|---|---|---|
| Mean ± StDev | 15.60 ± 3.50 | 5.67 ± 1.52 | 0.14 ± 0.04 | 2.05 ± 0.14 |
| 25th Percentile | 12.91 | 4.59 | 0.10 | 1.90 |
| Median | 15.57 | 5.90 | 0.13 | 2.04 |
| 75th Percentile | 19.20 | 6.94 | 0.17 | 2.17 |
| SEM | 1.17 | 0.51 | 0.01 | 0.05 |
| Normality | Normal | Normal | Normal | Normal | iii. Uniaxial Tension Testing to Failure

Figures 8A, 8B, 8C, 8D, 8E, 8F:
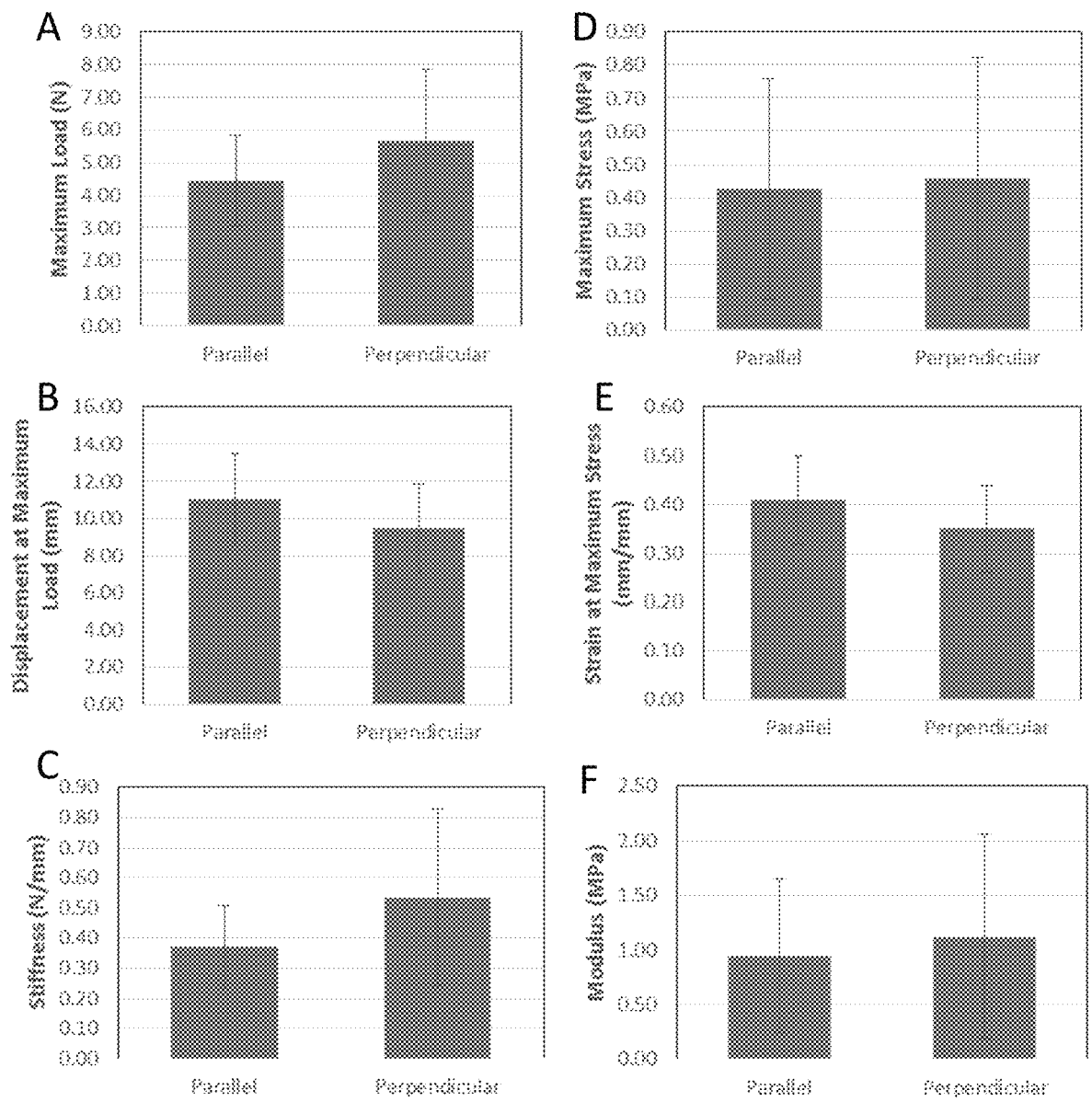
FIGS. 8A-8F show the umbilical tissue structural and material properties with respect to fiber orientation (Mean±StDev).

In 15 of 18 (83.3%) specimens, failure occurred in the tissue midsubstance away from the grips. For the remaining three specimens that had failures near the grip, the results of the biomechanical analysis were consistent with the midsubstance failure data and therefore they were included in the study. Data are reported in Tables 6 (parallel orientation) 7 (perpendicular orientation) and shown graphically in FIGS. 8A-8F, with structural properties shown in FIGS. 8A-8C and material properties shown in FIGS. 8D-8F.

TABLE 6

Uniaxial Tension Results - Parallel fiber orientation.

| | PARALLEL FIBER ORIENTATION | | | | | | |
|---|---|---|---|---|---|---|---|
| | Structural Properties | | | | Material Properties | | |
| | Cross-Sectional Area (mm²) | Maximum Load (N) | Displacement at Maximum Load (mm) | Stiffness (N/mm) | Maximum Stress (MPa) | Strain at Maximum Stress (mm/mm) | Modulus (MPa) |
| Mean ± StDev | 12.22 ± 2.79 | 4.45 ± 1.38 | 11.03 ± 2.47 | 0.43 ± 0.33 | 0.41 ± 0.09 | 0.95 ± 0.71 | 0.37 ± 0.14 |
| 25th Percentile | 11.387 | 3.482 | 9.720 | 0.280 | 0.360 | 0.506 | 0.268 |
| Median | 12.764 | 4.139 | 10.727 | 0.300 | 0.397 | 0.731 | 0.392 |
| 75th Percentile | 14.524 | 4.532 | 13.484 | 0.399 | 0.499 | 1.002 | 0.423 |
| SEM | 0.929 | 0.460 | 0.823 | 0.112 | 0.030 | 0.236 | 0.046 |
| Normality | Non-Parametric | Non-Parametric | Normal | Non-Parametric | Normal | Non-Parametric | Normal |

TABLE 7

Uniaxial Tension Results - Perpendicular fiber orientation.

| | PERPENDICULAR FIBER ORIENTATION | | | | | | |
|---|---|---|---|---|---|---|---|
| | Structural Properties | | | | Material Properties | | |
| | Cross-Sectional Area (mm²) | Maximum Load (N) | Displacement at Maximum Load (mm) | Stiffness (N/mm) | Maximum Stress (MPa) | Strain at Maximum Stress (mm/mm) | Modulus (MPa) |
| Mean ± StDev | 14.91 ± 4.53 | 5.66 ± 2.19 | 9.45 ± 2.4 | 0.46 ± 0.37 | 0.35 ± 0.09 | 1.12 ± 0.93 | 0.53 ± 0.29 |
| 25th Percentile | 11.993 | 4.192 | 8.245 | 0.242 | 0.305 | 0.502 | 0.321 |

TABLE 7-continued

Uniaxial Tension Results - Perpendicular fiber orientation.

| | PERPENDICULAR FIBER ORIENTATION | | | | | | |
|---|---|---|---|---|---|---|---|
| | | Structural Properties | | | Material Properties | | |
| | Cross-Sectional Area (mm$^2$) | Maximum Load (N) | Displacement at Maximum Load (mm) | Stiffness (N/mm) | Maximum Stress (MPa) | Strain at Maximum Stress (mm/mm) | Modulus (MPa) |
| Median | 16.304 | 5.638 | 9.099 | 0.267 | 0.337 | 0.904 | 0.648 |
| 75$^{th}$ Percentile | 17.244 | 6.609 | 10.467 | 0.489 | 0.388 | 1.650 | 0.758 |
| SEM | 1.509 | 0.730 | 0.801 | 0.122 | 0.030 | 0.311 | 0.098 |
| Normality | Normal | Normal | Normal | Non-Parametric | Normal | Normal | Normal |

3. CONCLUSIONS

The purpose of this study was to characterize various biomechanical properties of an umbilical tissue-based product using three testing modalities, which is needed since limited data exists in the literature. In general, the tissue had good handling qualities and there were no complications with specimen gripping for any of the performed tests. For all tests, tissue failure loads were within the operational range of the 100N load cell. In tests where specifically-oriented tissues were characterized (suture retention and uniaxial tension), there did not appear to be major biomechanical differences due to orientation (statistical comparisons were not included as part of this study).

The maximum stress values measured in this study were 0.41±0.09 MPa, while the strain at maximum stress was 0.95±0.71.

J. Viable Cryopreserved Umbilical Tissue (vCUT) Improves Soft Tissue Regeneration: Six Tendon Repair Case Reports Six patients underwent vCUT facilitated tendon repair procedures. Demographics include patients of 19 to 58 years of age with 4 female and 2 male patients. One patient had undergone an acute Achilles tendon repair, two had calcaneal exostectomy/haglunds excision with debridement/repair of Achilles, two underwent peroneus brevis repair, and one had a kidner with debridement/repair of posterior tibial tendon. Conservative therapy, consisting of rest, activity modification, trial of durable medical equipment, and physical therapy, was applied to all patients before grafting with vCUT. None of the patients developed infection post-surgery.

1. Achilles Repair, Acute and Chronic
i. Case 1

A 28-year-old male suffered a complete rupture of the right Achilles tendon while playing basketball. The patient underwent a V to Y recession with end to end repair of the tendon with Ethibond using a Krakow suture technique. The tendon was then wrapped with vCUT. Upon closing, Adaptic and a dry sterile dressing (DSD) were applied at the site and the patient was placed in a below the knee non weight bearing cast and given crutches. When the patient came back for follow up after one week post-surgery he reported little to no pain and his range of motion was minus 5 degrees of dorsiflexion. At four weeks post-operatively the patient's range of motion was 0 degrees of dorsiflexion. 6 weeks after the procedure the cast was removed and the patient was placed into a Controlled Ankle Movement (CAM) boot boot and began physical therapy 3 times a week for 4 weeks. At 8 weeks post-operatively the patient had a range of motion of positive 5 degrees of dorsiflexion, he transitioned into normal shoes, and was released back to work, reporting no pain.

ii. Case 2

A 44-year-old female presented with a painful Haglund's deformity with bursitis and Achilles tendonitis in her right foot. An excision of the Haglund's deformity and the right bursa was performed along with debridement of the right Achilles tendon. The Achilles tendon was then wrapped with vCUT and secured with Vicryl. After closure, Adaptic non-adherent dressing and a dry sterile dressing (DSD) were applied, and the patient was placed in a non-weight bearing cast and given crutches for off-loading. One week after surgery the patient reported little to no pain. At 2 weeks postoperative the cast was removed, and the patient was placed in a CAM boot. At 4 weeks postoperative, the incision line was barely visible. The patient was permitted to transition into normal shoe gear as tolerated and was given a prescription for physical therapy. At 8 weeks postoperative, no swelling was appreciated. She regained 100% muscle strength and continued physical therapy.

2. Achilles Tendonitis/Tenosynovitis
i. Case 3:

A 58 year-old female presented with painful Haglund's deformity of the left foot, along with a heel spur and Achilles tendonitis/ tenosynovitis. After failing conservative therapy, the patient was referred for surgery and underwent a resection of heel spur with debridement and anchoring of the Achilles tendon. vCUT was laid over the repaired Achilles prior to closure. A DSD was applied, and the patient was placed in a below-the-knee cast and given crutches for off-loading. One week postoperatively the incision line was flat with minimal swelling. At two weeks post-op, no complications was reported. The patient reported a 2/10 pain level 3 weeks postoperative, with no swelling, no dehiscence, and no infection. She was in a below-the-knee cast for three weeks and then placed into a CAM boot and allowed to weight bear to tolerance. She started her physical therapy at week 4.

3. Peroneus Brevis Tendon Repair
i. Case 4

A 19-year-old male with a partial tear of the left peroneus brevis tendon and anterior talofibular ligament injury in the left ankle. The patient had a past medical history of multiple vertigo, which resulted in multiple left ankle sprains. The patient underwent a repair and tubularization of the peroneus brevis tendon, a modified Brostrom, and the excision of low lying muscle belly. The tendon was wrapped with vCUT, and additional vCUT was laid over the Brostrom repair prior to closure. The patient was placed in a non-weight bearing cast of the left lower extremity. The patient experienced minimal to no pain the first week after surgery. No edema, erythema, or signs of infection was observed. The cast was removed at 4 weeks, and the patient was placed in a CAM boot and started physical therapy 3 times a week for 4 weeks. Minimal scarring at the incision site was observed at 4 weeks post-op. The patient was ambulating in a shoe at six weeks postoperative. At 7 weeks post-surgery, no scarring was observed. He healed faster with less pain, swelling, and scarring than previous procedures performed without vCUT.

ii. Case 5

A 47 year-old diabetic female presented with an MRI confirmation of a Peroneus Brevis tendon tear in the left ankle. The patient underwent a debridement and repair of the tendon. The tendon was tubularized and then wrapped with vCUT and secured with Vicryl. After primary closure, an additional piece of vCUT was placed subcutaneously followed by skin closure. Adaptic non-adherent dressing and a DSD were applied, and the patient was placed in a non-weight-bearing below-the-knee cast. The patient reported pain levels of 4/10 during the first week postoperative and no swelling was observed at the incision line. Her pain level was reduced to 2/10 pain levels the second week postoperative, and by 4 weeks postoperative, the patient reported no pain. The patient had weekly cast changes for 3 weeks and then transitioned into a CAM boot. Six weeks postoperative, there was little scarring at the incision site, and she was instructed to transition into a normal shoe as tolerated. At 10 week post-surgery, the scarring at the surgery site continued to diminish.

4. Posterior Tibial Tendon Repair i. Case 6

A 38-year-old female presented with left posterior tibial fraying/ posterior tibial tendon dysfunction. The patient ambulated with the aid of an ankle foot orthosis (AFO). Additionally the patient's medical history included a left sided drop foot and hypertrophic navicular causing an area of irritation and preulceration medical in the left foot. A resection of the hypertrophic navicular with debridement of the posterior tibial tendon and anchoring of tendon to navicular with a bone anchor was performed. vCUT was applied to the posterior tibial tendon and secured with Vicryl. Adaptic non-adherent dressing and a DSD were applied, and the patient was placed in a non-weight bearing cast and given crutches for off-loading. At one week after the procedure the patient reported no pain. The cast was removed at 4 weeks postoperative and the patient was placed in a CAM boot. Also at 4 weeks, the area of irritation from the AFO was resolving and the incision was healed. By 8 weeks postoperative the area of irritation had continued to improve with some discoloration. At 13 week post-op visit, the dark discoloration continued to regain normal pigmentation.

5. Discussion

The results show that adjunctive use of viable cryopreserved umbilical tissue in a variety of tendon repair surgeries is both safe and effective. Furthermore, the results indicate that the viable cryopreserved umbilical tissue was able to significantly improve patient pain level, speed up the repair process, and minimize scarring, which allows them to resume daily and recreational activities without limitation and mostly, or completely, free of pain.

K. Adhesion Barrier Rabbit Model

Rabbits were anesthetized with ketamine and xylazine. Additionally, Buprenorphine (0.03 mg/kg) was administered. An IV catheter was placed in a marginal ear vein and rabbit's abdomen was shaved. In the operating room an endotracheal tube was placed. During surgery rabbits were maintained under anesthesia with 1-3% isoflurane+1-2 Lt oxygen. A pulse oximeter was used to monitor heart rate and SpO2. Temperature was monitored every 15 min when possible. Prior to initiation of the procedure the surgical field was aseptically scrubbed with betadine scrub solution and rinsed with 70% ethanol for three times.

A 10 cm midline laparotomy was made and the cecum and bowel excised after draping the surgical field with sterile surgical drape. The surface of the cecum adjacent to the sidewall defect was abraded with sterile gauze for 15 minutes until petechial hemorrhage was observed. The surface of the cecum facing the rest of the bowel was also abraded for 5 minutes. Abdominal wall was abraded by removing a portion of the muscle layer to induce bleeding and inflammation. After the completion of the adhesion creation, the bowel was replaced into the abdominal cavity and the abdomen was closed. For the treatment group prior to the abdominal closure viable cryopreserved umbilical tissue (CUT) was sutured to the abdominal wall followed by suturing the cecum to the abdominal wall for direct (and continuous) contact of the abraded tissue to the wall. Abdomen was closed. Body weight for each animal was taken weekly. Cage side observations were conducted once daily to monitor the general health status of the animals. On days 7, 28 and 74 animals were euthanized with the use of sodium pentobarbital while under ketamine Xylazine anesthesia. Experimental design is summarized in Table 8.

TABLE 8

Experiment Design to Evaluate Anti-Fibrotic Effect of Viable Cryopreserved Umbilical Cord Tissue (CUT)

| Group | Procedure to induce adhesion formation | Number of adhesion sites per animal | Treatment type per site | Evaluation time point post surgery | | |
|---|---|---|---|---|---|---|
| | | | | day 7 | day 28 | day 74 |
| 1 | Cecum abrasion | 2 | CUT/Control | Animal 1 | Animal 9 | Animal 15 |
| | | | | Animal 2 | Animal 10 | Animal 16 |
| 2 | Cecum abrasion with suture of cecum to abdomen | 1 | CUT | Animal 4 | Animal 11 | Animal 13 |
| 3 | Cecum abrasion | 2 | CUT/CUT | Animal 5 | Animal 12 | — |
| 4 | Cecum abrasion | 2 | Control/Control | Animal 3 | Animal 7 | — |

TABLE 8-continued

Experiment Design to Evaluate Anti-Fibrotic Effect of Viable Cryopreserved Umbilical Cord Tissue (CUT)

| Group | Procedure to induce adhesion formation | Number of adhesion sites per animal | Treatment type per site | Evaluation time point post surgery | | |
|---|---|---|---|---|---|---|
| | | | | day 7 | day 28 | day 74 |
| 5 | Cecum abrasion with suture of cecum to abdomen | 1 | Control | Animal 6 | Animal 14 | Animal 8 |

The abraded abdominal wall directly opposed to the cecum showed early signs of adhesion formation by 7 days. These adhesions involved multiple bowel segments. In the presence of CUT, there were no adhesions detected in the area covered by CUT. Minor adhesions were noted only around edges that were not covered by CUT. Significant local hemorrhage was still present due to surgery. The abdominal wall that was sutured to the abraded cecum resulted in strong adhesion formation observed at 7 days post surgery. In the presence of CUT, adhesions between cecum and abdominal wall were not detected. However, the abraded uncovered by CUT edges showed adhesion formation. Minor adhesion detected between CUT and abraded cecum could be due to inflammation driven proteolysis of CUT.

Multiple sections of the cecum displayed tight adhesions to the abdominal wall. In the presence of CUT, there were no adhesion formation. Partial CUT degradation was observed. Cecum at the edge, which was not covered by CUT, had adhesions. The abdominal wall that was sutured to the abraded cecum resulted in strong adhesion formation at multiple segments. No adhesions between cecum and abdominal wall in the presence of CUT were detected. However, the abraded uncovered edges of cecum and abdominal wall around CUT have adhesions.

Sections of the cecum displayed tight adhesion to the abdominal wall. In the presence of CUT, there were no signs of adhesion. Also, CUT over a period of 74 days had completely dissipated with reminiscent of the tissue on the abdominal wall. There was presence of no marked inflammation and complete absence of adhesion between abdominal wall and cecum. The abdominal wall that was sutured to the abraded cecum still had very strong adhesion. No adhesion was observed between the sutured abdominal wall to the cecum. CUT had almost completely dissolved with very little presence of CUT on the abdominal wall.

L. Antimicrobial Effects of Viable Cryopreserved Umbilical Tissue (CUT) in a Rat Model of Post-Surgical Infection Adhesions and infection are serious complications of abdominal reconstructive surgeries using synthetic meshes. Infection has been reported in as many as 30% of cases after mesh use in contaminated operative abdominal fields regardless of the material used. The purpose of this study is to evaluate viable cryopreserved umbilical tissue for prevention of post-surgical infection in Sprague Dawley Rats.

Rats undergo surgery to generate subcutaneous infections to test the ability of candidate barriers to prevent post-surgical infection.

Prior to surgery, rats can be anesthetized with ketamine and xylazine. Buprenorphine can be administered. The dorsal surface can be shaved or a depilatory used to remove unwanted hair and the animal can be maintained under injectable anesthesia and supplemented with isoflurane if necessary. The surgical site can be surgically scrubbed with Nolvasane scrub or betadine scrub solution and rinsed with 70% ethanol at least 2-3 times.

Bilateral 3-cm dorsal incisions can be made 1 cm lateral to the spine. A subcutaneous pocket can be created at each incision site and 1 test article (of the same type and inoculum) can be placed into each pocket. The bacterial inoculum (~200 μL) or sterile saline (~200 μL) can be pipetted onto each implanted test article before skin closure with sterile staples, or suture and/or tissue adhesive. Gross and histological evaluation can be performed after 28 days. Study groups are described in table 9.

TABLE 9

Description of the Study Groups

| No of animals per group | Sites | Treatment type | Bacteria type |
|---|---|---|---|
| 7 | 2 | CUT | E. coli |
| 7 | 2 | CUT | S. aureus |
| 7 | 2 | none | E. coli |
| 7 | 2 | none | S. aureus |
| 7 | 2 | Collagen dressing | E. coli |

The dorsum of the rat was shaved to expose the skin for surgery. A 3×3 cm incision was made to introduce a subcutaneous pouch. Subcutaneous implantation in the dorsum with 2.5×2.5 cm CUT was followed by the inoculation with 2 different strains of bacteria. *Staphylococcus aureus* ATCC 6538 at a concentration of $1 \times 10^3$ CFU/wound and *Escherichia coli* ATCC 25922 at a concentration of $7 \times 10^5$ CFU/wound was used. Following surgery the incisioned dorsum was sutured. The evaluation and collection of the subcutaneous implantation of test material and bacteria was done post 28 days.

Those skilled in the art will recognize, or be able to ascertain using no more than routine experimentation, many equivalents to the specific embodiments of the method and compositions described herein. Such equivalents are intended to be encompassed by the following claims.

REFERENCES

1. ASTM D6797-02—Standard Test Method for Bursting Strength of Fabrics: Constant-rate-of-extension (CRE) Ball Burst
2. Biaxial strength of multilaminated extracellular matrix scaffolds. Freytes D O, Badylak S F, Webster T J, Geddes L A, Rundell A E. Biomaterials, 2004 (25), 12,2353-61

3. Biomechanical properties of the human umbilical cord. Pennati G. Biorheology, 2001 (38), 355-366

We claim:

1. A method of making an umbilical tissue composition, the method comprising:
   (a) isolating umbilical tissue from a subject; and
   (b) forming one or more engineered channels through at least a portion of the umbilical tissue.

2. The method of claim 1, further comprising removing blood vessels from the umbilical tissue.

3. The method of claim 2, wherein said removing causes the umbilical tissue to be devoid of the two arteries and one vein originally present in the umbilical tissue.

4. The method of claim 1, further comprising removing, depleting, and/or killing immunogenic cells in the umbilical tissue.

5. The method of claim 4, wherein said removing, depleting, and/or killing causes the umbilical tissue to be devoid of viable immunogenic cells.

6. The method of claim 1, further comprising cryopreserving the umbilical tissue.

7. The method of claim 6, wherein the cryopreserved umbilical tissue comprises viable cells native to the umbilical tissue, wherein the viable cells comprise mesenchymal stem cells, fibroblasts, epithelial cells, or a combination thereof.

8. The method of claim 6, wherein the umbilical tissue comprises one or more growth factors native to the umbilical tissue and/or one or more cytokines native to the umbilical tissue.

9. The method of claim 1, wherein the umbilical tissue comprises a Wharton's jelly layer side and an amniotic epithelial layer side, wherein the one or more engineered channels are formed on the Wharton's jelly layer side and do not extend through the amnion side.

10. The method of claim 1, wherein the one or more engineered channels are formed through the entire umbilical tissue.

11. The method of claim 1, further comprising treating the umbilical tissue with at least one antibiotic.

12. The method of claim 1, further comprising removing substantially all the umbilical cord blood from the umbilical tissue.

13. The method of claim 1, wherein forming the one or more engineered channels comprises removal of umbilical cord tissue by mechanical means or by laser.

14. The method of claim 1, wherein forming the one or more engineered channels comprises displacement of umbilical cord tissue.

* * * * *